Figure 1:
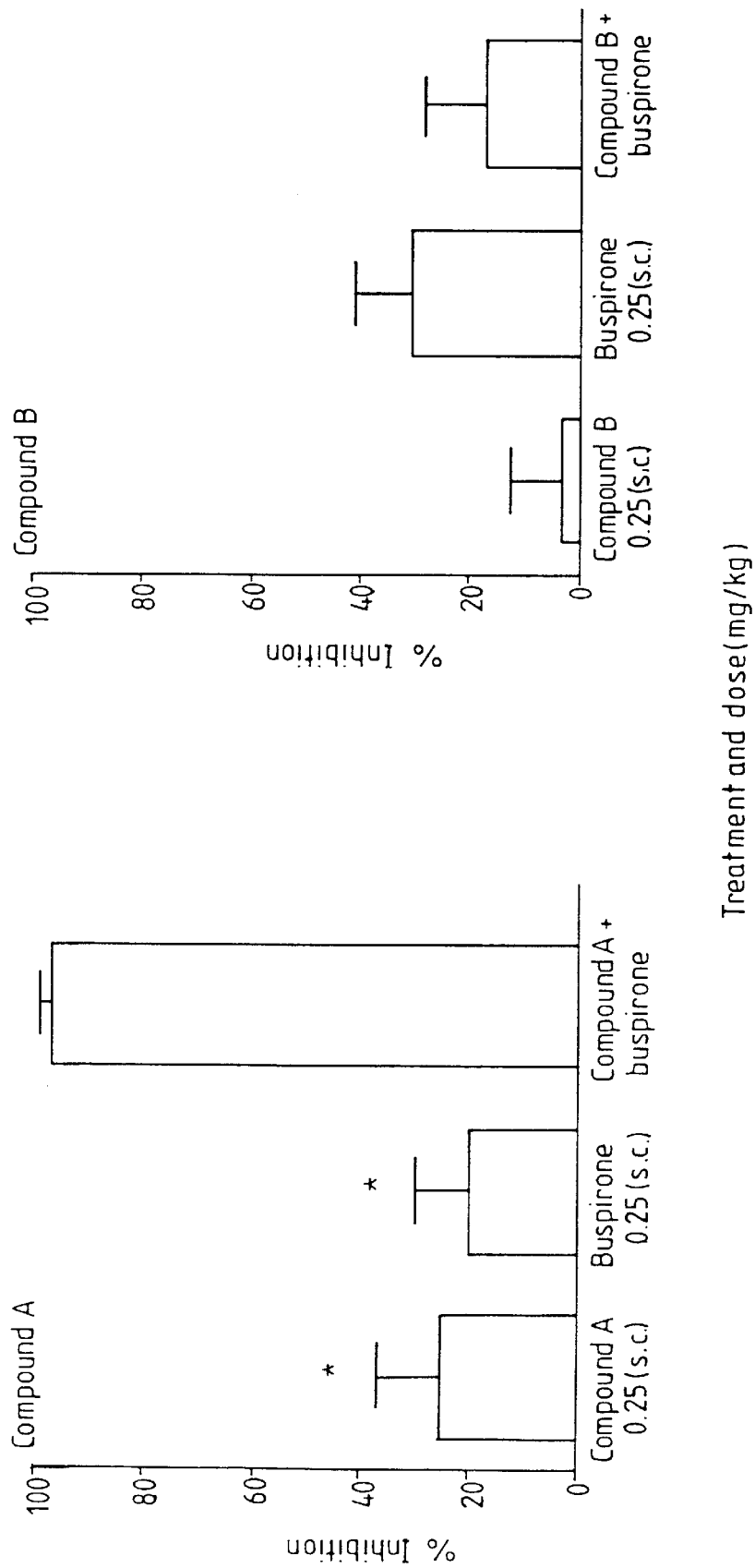
Figure 2:
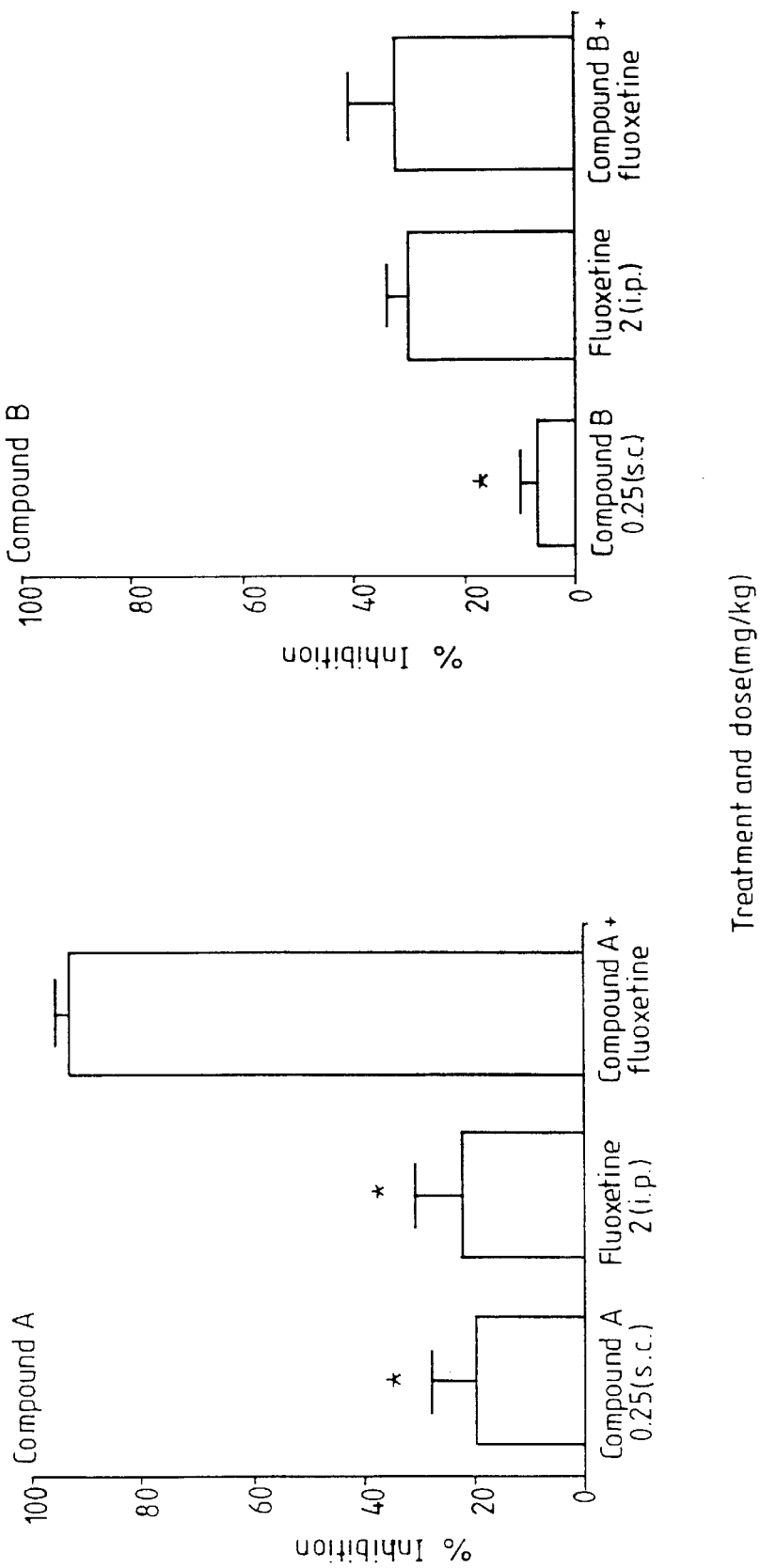

«12» United States Patent
Hefti

«11» Patent Number: 6,162,805
«45» Date of Patent: Dec. 19, 2000

[54] USE OF AN NK-1 RECEPTOR ANTAGONIST AND AN SSRI FOR TREATING OBESITY

[75] Inventor: Franz Fridolin Hefti, Much Hadham, United Kingdom

[73] Assignee: Merck Sharp & Dohme Limited, Hoddesdon, United Kingdom

[21] Appl. No.: 09/403,519

[22] PCT Filed: Apr. 22, 1998

[86] PCT No.: PCT/GB98/01178

§ 371 Date: Oct. 22, 1999

§ 102(e) Date: Oct. 22, 1999

[87] PCT Pub. No.: WO98/47514

PCT Pub. Date: Oct. 29, 1998

[30] Foreign Application Priority Data

Apr. 24, 1997 [GB] United Kingdom .................... 9708288
Oct. 7, 1997 [GB] United Kingdom .................... 9721266

[51] Int. Cl.[7] ...................... A61K 31/535; A61K 31/445; A61K 31/135; A61K 31/075
[52] U.S. Cl. ...................... 514/236.2; 514/910; 514/321; 514/657; 514/716; 514/909
[58] Field of Search .................... 514/236.2, 321, 514/657, 716, 909, 910

[56] References Cited

FOREIGN PATENT DOCUMENTS

| 0 747 049 | 12/1996 | European Pat. Off. . |
| WO 96/24353 | 8/1996 | WIPO . |
| WO 96/34877 | 11/1996 | WIPO . |
| WO 96/37207 | 11/1996 | WIPO . |
| WO 97/38692 | 10/1997 | WIPO . |

OTHER PUBLICATIONS

CA 105:218899, abstract of JP 61148121 A2, Jul. 1986.
CA 115:270439, Pijl et al., 1991.
CA 126:152744, Ricca et al., 1996.

Primary Examiner—Kimberly Jordan
Attorney, Agent, or Firm—J. Eric Thies; David L. Rose

[57] ABSTRACT

The present invention relates to the use of an NK-1 receptor antagonist and a selective serotonin reuptake inhibitor for the treatment or prevention of obesity.

8 Claims, 2 Drawing Sheets

USE OF AN NK-1 RECEPTOR ANTAGONIST AND AN SSRI FOR TREATING OBESITY

This application is a 371 of PCT/GB98/01178, filed Apr. 22, 1998.

This invention relates to the treatment or prevention of obesity by the administration of a combination of a NK-1 receptor antagonist and a selective serotonin reuptake inhibitor.

Obesity is a chronic disease that is highly prevalent in modern society and is associated not only with a social stigma, but also with decreased life span and numerous medical problems, including adverse psychological development, reproductive disorders such as polycystic ovarian disease, dermatological disorders such as infections, varicose veins, *Acanthosis nigricaits*, and eczema, exercise intolerance, diabetes mellitus, insulin resistance, hypertension, hypercholesterolemia, cholelithiasis, osteoarthritis, orthopedic injury, thromboembolic disease, cancer, and coronary heart disease. Rissanen et al, *British Medical Journal*, 301:835–837 (1990).

Treatment regimens for obesity typically include the use of selective serotonin reuptake inhibitors (SSRIs). SSRIs alter the synaptic availability of serotonin through their inhibition of presynaptic reaccumulation of neuronally released serotonin. The SSRI, fluoxetine, has found to be of use in the treatment of obesity.

Neurokinin 1 (NK-1; substance P) receptor antagonists are being developed for the treatment of a number of physiological disorders associated with an excess or imbalance of tachykinins, and in particular substance P. Examples of such conditions include disorders of the central nervous system such as anxiety, depression and psychosis (see, for instance, International (PCT) patent specification Nos. WO 95/16679, WO 95/18124 and WO 95/23798).

International (PCT) patent specification No. WO 96/24353 published Aug. 15, 1996) claims methods for the treatment of psychiatric disorders using a combination of a tachykinin antagonist and a serotonin agonist or selective serotonin reuptake inhibitor referring inter alia to bulimia nervosa. However, the disclosure of WO 96/24353 does not provide any teaching as to whether the claimed combination has any efficacy and in particular there is no direction towards specific combinations which might treat obesity.

There is therefore a need for a combination of an SSRIs with a NK-1 receptor antagonist, which combination provides an unexpected and advantageous effect in treating obesity. Such combinations may for example provide an enhanced anti-obesity effect. They may also provide for a rapid onset of action to combat obesity thereby enabling prescription on an "as-needed" basis.

A particularly preferred class of NK-1 receptor antagonists of use in the present invention are those which are able to cross the blood-brain barrier otherwise known as CNS- or brain-penetrant compounds. CNS-penetrant NK-1 receptor antagonists have been found to potentiate the pharmacological effects of fluoxetine. While not being bound to any particular theory of operation, an enhanced effect at treating or preventing a psychological stress response in an animal assay is observed with the combination of drugs than would be expected from either drug alone. In particular, combination therapy of a CNS-penetrant NK-1 receptor antagonist and a selective serotonin reuptake inhibitor effectively inhibits separation-induced vocalisations in guinea-pig pups. Such unexpected results would not have been predicted based on the disclosures in the art.

The present invention accordingly provides the use of a NK-1 receptor antagonist and an SSRI for the manufacture of a medicament for the treatment or prevention of obesity.

The present invention also provides a method for the treatment or prevention of obesity, which method comprises administration to a patient in need of such treatment an amount of a NK-1 receptor antagonist and an amount of an SSRI, such that together they give effective relief.

In a further aspect of the present invention, there is provided a pharmaceutical composition for the treatment or prevention of obesity comprising a NK-1 receptor antagonist and an SSRI, together with at least one pharmaceutically acceptable carrier or excipient.

It will be appreciated that the NK-1 receptor antagonist and SSRI, may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a NK-1 receptor antagonist and an SSRI as a combined preparation for simultaneous, separate or sequential use in the treatment or prevention of obesity.

In an alternative embodiment of the present invention, there is provided the use of a NK-1 receptor antagonist and an SSRI for the manufacture of a medicament for reducing the total body fat mass in an obese mammal, especially a human.

The present invention also provides a method for reducing the total body fat mass in an obese mammal, especially a human, which method comprises administration to the mammal an amount of a NK-1 receptor antagonist and an amount of an SSRI, such that together they give effective relief.

In a further aspect of the present invention, there is provided a pharmaceutical composition for reducing the total body fat mass in an obese mammal, especially a human, comprising a NK-1 receptor antagonist and an SSRI, together with at least one pharmaceutically acceptable carrier or excipient.

It will be appreciated that the NK-1 receptor antagonist and SSRI, may be present as a combined preparation for simultaneous, separate or sequential use for reducing the total body fat mass in an obese mammal, especially a human. Such combined preparations may be, for example, in the form of a twin pack.

In a further or alternative aspect of the present invention there is therefore provided a product comprising a NK-1 receptor antagonists and an SSRI as a combined preparation for simultaneous, separate or sequential use in reducing the total body fat mass in an obese mammal, especially a human.

It will be appreciated that when using a combination of the present invention, both the NK-1 receptor antagonist and the SSRI will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the SSRI may be administered as a tablet and then, within a reasonable period of time, the NK-1 receptor antagonist may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the SSRI is provided as a tablet, then within one hour, the NK-1 receptor antagonist should be administered, either in the same type of dosage form, or another dosage form which provides effective delivery of the medicament.

As used herein "obesity" refers to a condition whereby a mammal has a Body Mass Index (BMI), which is calculated as weight per height squared (kg/m$^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. "Treatment" refers to reducing the BMI of the mammal to less than about 25.9, and maintaining that weight for at least 6 months. The treatment suitably results in a reduction in food or calorie intake by the mammal.

"Prevention" refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycycstic ovarian disease, cardiovascular diseases, osteoarthritis, dermatological disorders, hypertension, insulin resistance, hypercholesterolemia, hypertriglyceridemia, and cholelithiasis.

Thus, in one aspect, this invention relates to the inhibition and/or complete suppression of lipogenesis in obese mammals, i.e., the excessive accumulation of lipids in fat cells, which is one of the major features of human and animal obesity, as well as loss of total body weight. In another aspect, the invention ameliorates the conditions that are a consequence of the disease, such as preventing or arresting the progression of polycystic ovarian disease so that the patient is no longer infertile, and increasing the insulin sensitivity and/or decreasing or eliminating the need or usage of insulin in a diabetic patient, e.g., one with adult-onset diabetes or Type II diabetes.

"Mammals" include animals of economic importance such as bovine, ovine, and porcine animals, especially those that produce meat, as well as domestic animals, sports animals, zoo animals, and humans, the latter being preferred.

The compositions of the present invention are especially useful for the treatment of or prevention of obesity where the use of an SSRI is generally prescribed. By the use of a combination of a NK-1 receptor. antagonist and an SSRI in accordance with the present invention, it is now also possible to treat or prevent obesity in patients for whom conventional anti-obesity therapy might not be wholly successful or where dependance upon the anti-obesity therapy is prevalent.

Suitable selective serotonin reuptake inhibitors of use in the present invention include: fluoxetine, fluvoxamine, paroxetine and sertraline, and pharmaceutically acceptable salts thereof.

NK-1 receptor antagonists of use in the present invention are described in published European Patent Specification Nos. 0 360 390, 0 394 989, 0 429 366, 0 443 132, 0 482 539, 0 512 901 0 512 902, 0 514 273, 0 514 275, 0 517 589, 0 520 555, 0 522 808, 0 528 495, 0 532 456, 0 533 280, 0 536 817, 0 545 478, 0 577 394, 0 590 152, 0 599 538, 0 610 793, 0 634 402, 0 686 629, 0 693 489, 0 694 535, 0 699 655, 0 699 674, 0 707 006, 0 708 101, 0 714 891, 0 723 959, 0 733 632 and 0 776 893; and in International Patent Specification Nos. 90/05525, 90/05729, 91109844, 91/18899, 92/01688, 92/06079, 92/12151, 92/15585, 92/17449, 92/20661, 92/20676, 92/21677, 93/00330, 93/00331, 93/01159, 93/01165, 93101169, 93/01170, 93/06099, 93/09116, 93/10073, 93/14113, 93/18023, 93/19064, 93/21155, 9321181, 93/23380, 93/24465, 94/01402, 94/02461, 94/03429, 94/03445, 94104494, 94/04496, 94/05625, 94/07843, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95104040, 95/04042, 95106645, 95107886, 95/07908, 95/08549, 95/11880, 95/14017, 95/415311, 95/16679, 95/17382, 95/18124, 95/18129, 95/19344, 95/20575, 95/21819, 96/22525, 95/23798, 95/26338, 95/28418, 95/30674, 95/30687, 96/05193, 96/05203, 96/06094, 96/07649, 96/10562, 96/16939, 96/18643, 96/20197, 96/21661, 96/29304, 96/29317, 96129326, 96129328, 96/31214, 96/32385, 96/37489, 97/01553, 97/01554, 97103066, 97/08144, 97/14671, 97/17362, 97/18206, 97/19084, 97/19942 and 97/21702; and in British Patent Specification Nos. 2 266 529, 2 268 931, 2 269 170, 2 269 590, 2 271 774, 2 292 144, 2 293 168, 2 293 169, and 2 302 689.

Particularly preferred NK-1 receptor antagonists are those described in European Patent Specification No. 0 577 394, i.e. compounds of formula (I):

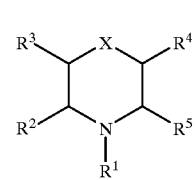

(I)

or a pharmaceutically acceptable salt thereof, wherein:
R$^1$ is selected from the group consisting of:
(1) hydrogen;
(2) C$_{1-6}$alkyl, unsubstituted or substituted with one or more of the substituents selected from:
  (a) hydroxy,
  (b) oxo,
  (c) C$_{1-6}$alkoxy,
  (d) phenyl-C$_{1-3}$alkoxy,
  (e) phenyl,
  (f) —CN,
  (g) halo,
  (h) —NR$^9$R$^{10}$, wherein R$^9$ and R$^{10}$ are independently selected from:
    (i) hydrogen,
    (ii) C$_{1-6}$alkyl,
    (iii) hydroxy-C$_{1-6}$alkyl, and
    (iv) phenyl,
  (i) —NR$^9$COR$^{10}$, wherein R$^9$ and R$^{10}$ are as defined above,
  (j) —NR$^9$CO$_2$R$^{10}$, wherein R$^9$ and R$^{10}$ are as defined above,
  (k) —CONR$^9$R$^{10}$, wherein R$^9$ and R$^{10}$ are as defined above,
  (l) —COR$^9$, wherein R$^9$ is as defined above,
  (m) —CO$_2$R$^9$, wherein R$^9$ is as defined above,
  (n) heterocycle, wherein the heterocycle is selected from the group consisting of:

(A) benzimidazolyl,
(B) benzofuranyl,
(C) benzthiophenyl,
(D) benzoxazolyl,
(E) furanyl,
(F) imidazolyl,
(G) indolyl,
(H) isoxazolyl,
(I) isothiazolyl,
(J) oxadiazolyl,
(K) oxazolyl,
(L) pyrazinyl,
(M) pyrazolyl,
(N) pyridyl,
(O) pyrimidyl,
(P) pyrrolyl,
(Q) quinolyl,
(R) tetrazolyl,
(S) thiadiazolyl,
(T) thiazolyl,
(U) thienyl,
(V) triazolyl,
(W) azetidinyl,
(X) 1,4-dioxanyl,
(Y) hexahydroazepinyl,
(Z) oxanyl,
(AA) piperazinyl,
(AB) piperidinyl,
(AC) pyrrolidinyl,
(AD) tetrahydrofuranyl, and
(AE) tetrahydrothienyl,
and wherein the heterocylcle is unsubstituted or substituted with one or more substituent(s) selected from:
  (i) $C_{1-6}$alkyl, unsubstituted or substituted with halo, —$CF_3$, —$OCH_3$, or phenyl,
  (ii) $C_{1-6}$alkoxy,
  (iii) oxo,
  (iv) hydroxy,
  (v) thioxo,
  (vi) —$SR^9$, wherein $R^9$ is as defined above,
  (vii) halo,
  (viii) cyano,
  (ix) phenyl,
  (x) trifluoromethyl,
  (xi) —$(CH_2)_m$—$NR^9R^{10}$, wherein m is 0, 1 or 2, and $R^9$ and $R^{10}$ are as defined above,
  (xii) —$NR^9COR^{10}$, wherein $R^9$ and $R^{10}$ are as defined above,
  (xiii) —$CONR^9R^{10}$, wherein $R^9$ and $R^{10}$ are as defined above,
  (xiv) —$CO_2R^9$, wherein $R^9$ is as defined above, and
  (xv) —$(CH_2)_m$—$OR^9$, wherein m and $R^9$ are as defined above;
(3) $C_{2-6}$alkenyl, unsubstituted or substituted with one or more of the substituent(s) selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$CONR^9R^{10}$, wherein $R^9$ and $R^{10}$ are as defined above,
  (i) —$COR^9$, wherein $R^9$ is as defined above,
  (j) —$CO_2R^9$, wherein $R^9$ is as defined above,
  (k) heterocycle, wherein the heterocycle is as defined above;
(4) $C_{2-6}$alkynyl;
(5) phenyl, unsubstituted or substituted with one or more of the substituent(s) selected from:
  (a) hydroxy,
  (b) $C_{1-6}$alkoxy,
  (c) $C_{1-6}$alkyl,
  (d) $C_{2-5}$alkenyl,
  (e) halo,
  (f) —CN,
  (g) —$NO_2$,
  (h) —$CF_3$,
  (i) —$(CH_2)_m$—$NR^9R^{10}$, wherein m, $R^9$ and $R^{10}$ are as defined above,
  (j) —$NR^9COR^{10}$, wherein $R^9$ and $R^{10}$ are as defined above,
  (k) —$NR^9CO_2R^{10}$, wherein $R^9$ and $R^{10}$ are as defined above,
  (l) —$CONR^9R^{10}$, wherein $R^9$ and $R^{10}$ are as defined above,
  (m) —$CO_2NR^9R^{10}$, wherein $R^9$ and $R^{10}$ are as defined above,
  (n) —$COR^9$, wherein $R^9$ is as defined above,
  (o) —$CO_2R^9$, wherein $R^9$ is as defined above;
$R^2$ and $R^3$ are independently selected from the group consisting of:
(1) hydrogen;
(2) $C_{1-6}$alkyl, unsubstituted or substituted with one or more of the substituents selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$NR^9R^{10}$, wherein $R^9$ and $R^{10}$ are independently selected from:
  (i) —$NR^9COR^{10}$, wherein $R^9$ and $R^{10}$ are as defined above,
  (j) —$NR^9CO_2R^{10}$, wherein $R^9$ and $R^{10}$ are as defined above,
  (k) —$CONR^9R^{10}$, wherein $R^9$ and $R^{10}$ are as defined above,
  (l) —$COR^9$, wherein $R^9$ is as defined above, and
  (m) —$CO_2R^9$, wherein $R^9$ is as defined above;
(3) $C_{2-6}$alkenyl, unsubstituted or substituted with one or more of the substituent(s) selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$CONR^9R^{10}$ wherein $R^9$ and $R^{10}$ are as defined above,
  (i) —$COR^9$, wherein $R^9$ is as defined above, (j) —CO$_2$R$^9$, wherein R$^9$ is as defined above;
(4) C$_{2-6}$alkynyl;
(5) phenyl, unsubstituted or substituted with one or more of the substituent(s) selected from:
  (a) hydroxy,
  (b) C$_{1-6}$alkoxy,
  (c) C$_{1-6}$alkyl,
  (d) C$_{2-5}$alkenyl,
  (e) halo,
  (f) —CN,
  (g) —NO$_2$,
  (h) —CF$_3$,
  (i) —(CH$_2$)$_m$—NR$^9$R$^{10}$, wherein m, R$^9$ and R$^{10}$ are as defined above,
  (j) —NR$^9$COR$^{10}$, wherein R$^9$ and R$^{10}$ are as defined above,
  (k) —NR$^9$CO$_2$R$^{10}$, wherein R$^9$ and R$^{10}$ are as defined above,
  (l) —CONR$^9$R$^{10}$, wherein R$^9$ and R$^{10}$ are as defined above,
  (m) —CO$_2$NR$^9$R$^{10}$, wherein R$^9$ and R$^{10}$ are as defined above,
  (n) —COR$^9$, wherein R$^9$ is as defined above,
  (o) —CO$_2$R$^9$, wherein R$^9$ is as defined above;
and the groups R$^1$ and R$^2$ may be joined together to form a heterocyclic ring selected from the group consisting of:
  (a) pyrrolidinyl,
  (b) piperidinyl,
  (c) pyrrolyl,
  (d) pyridinyl,
  (e) imidazolyl,
  (f) oxazolyl, and
  (g) thiazolyl,
and wherein the heterocyclic ring is unsubstituted or substituted with one or more substituent(s) selected from:
  (i) C$_{1-6}$alkyl,
  (ii) oxo,
  (iii) C$_{1-6}$alkoxy,
  (iv) NR$^9$R$^{10}$, wherein R$^9$ and R$^{10}$ are as defined above,
  (v) halo, and
  (vi) trifluoromethyl;
and the groups R$^2$ and R$^3$ may be joined together to form a carbocyclic ring selected from the group consisting of
  (a) cyclopentyl,
  (b) cyclohexyl,
  (c) phenyl,
and wherein the carbocyclic ring is unsubstituted or substituted with one or more substituents selected from:
  (i) C$_{1-6}$alkyl,
  (ii) C$_{1-6}$alkoxy,
  (iii) —NR$^9$R$^{10}$, wherein R$^9$ and R$^{10}$ are as defined above,
  (iv) halo, and
  (v) trifluoromethyl;
and the groups R$^2$ and R$^3$ may be joined together to form a heterocyclic ring selected from the group consisting of:
  (a) pyrrolidinyl,
  (b) piperidinyl,
  (c) pyrrolyl,
  (d) pyridinyl,
  (e) imidazolyl,
  (f) furanyl,
  (g) oxazolyl,
  (h) thienyl, and
  (i) thiazolyl,
and wherein the heterocyclic ring is unsubstituted or substituted with one or more substituent(s) selected from:
  (i) C$_{1-6}$alkyl,
  (ii) oxo,
  (iii) C$_{1-6}$alkoxy,
  (iv) —NR$^9$R$^{10}$, wherein R$^9$ and R$^{10}$ are as defined above,
  (v) halo, and
  (vi) trifluoromethyl;
X is selected from the group consisting of:
  (1) —O—,
  (2) —S—,
  (3) —SO—, and
  (4) —SO$_2$—;
R$^4$ is selected from the group consisting of:

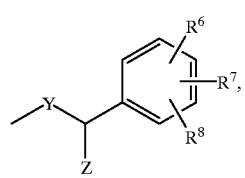

(2) —Y—C$_{1-8}$alkyl, wherein alkyl is unsubstituted or substituted with one or more of the substituents selected from:
  (a) hydroxy,
  (b) oxo,
  (c) C$_{1-6}$alkoxy,
  (d) phenyl-C$_{1-3}$alkoxy,
  (e) phenyl,
  (f) —CN,
  (g) halo,
  (h) —NR$^9$R$^{10}$, wherein R$^9$ and R$^{10}$ are as defined above,
  (i) —NR$^9$COR$^{10}$, wherein R$^9$ and R$^{10}$ are as defined above,
  (j) —NR$^9$CO$_2$R$^{10}$, wherein R$^9$ and R$^{10}$ are as defined above,
  (k) —CONR$^9$R$^{10}$, wherein R$^9$ and R$^{10}$ are as defined above,
  (l) —COR$^9$, wherein R$^9$ is as defined above,
  (m) —CO$_2$R$^9$, wherein R$^9$ is as defined above;
(3) —Y—C$_{2-6}$alkenyl, wherein the alkenyl is unsubstituted or substituted with one or more of the substituent(s) selected from:
  (a) hydroxy,
  (b) oxo,
  (c) C$_{1-6}$alkoxy,
  (d) phenyl-C$_{1-3}$alkoxy,
  (e) phenyl,
  (f) —CN,
  (g) halo,
  (h) —CONR$^9$R$^{10}$, wherein R$^9$ and R$^{10}$ are as defined above,
  (i) —COR$^9$, wherein R$^9$ is as defined above,
  (j) —CO$_2$R$^9$, wherein R$^9$ is as defined above,
(4) —O(CO)-phenyl, wherein the phenyl is unsubstituted or substituted with one or more of R$^6$, R$^7$and R$^8$;
R$^5$ is selected from the group consisting of:
(1) phenyl, unsubstituted or substituted with one or more of R$^{11}$, R$^{12}$ and R$^{13}$;
(2) C$_{1-8}$alkyl, unsubstituted or substituted with one or more of the substituent(s) selected from:
  (a) hydroxy,
  (b) oxo,
  (c) C$_{1-6}$alkoxy,
  (d) phenyl-C$_{1-3}$alkoxy, (e) phenyl,
(f) —CN,
(g) halo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above,
(m) —CO$_2$R$^9$, wherein R$^9$ is as defined above;
(3) C$_{2-6}$alkenyl, unsubstituted or substituted with one or more of the substituent(s) selected from:
(a) hydroxy,
(b) oxo,
(c) C$_{1-6}$alkoxy,
(d) phenyl-C$_{1-3}$alkoxy,
(e) phenyl,
(f) —CN,
(g) halo,
(h) —CONR$^9$R$^{10}$, wherein R$^9$ and R$^{10}$ are as defined above,
(i) —COR$^9$, wherein R$^9$ is as defined above,
(j) —CO$_2$R$^9$, wherein R$^9$ is as defined above;
(4) heterocycle, wherein the heterocycle is as defined above;
R$^6$, R$^7$ and R$^8$ are independently selected from the group consisting of:
(1) hydrogen;
(2) C$_{1-6}$alkyl, unsubstituted or substituted with one or more of the substituents selected from:
(a) hydroxy,
(b) oxo,
(c) C$_{1-3}$alkoxy,
(d) phenyl-C$_{1-3}$alkoxy,
(e) phenyl,
(f) —CN,
(g) halo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above, and
(m) —CO$_2$R$^9$, wherein R$^9$ is as defined above;
(3) C$_{2-6}$alkenyl, unsubstituted or substituted with one or more of the substituent(s) selected from:
(a) hydroxy,
(b) oxo,
(c) C$_{1-6}$alkoxy,
(d) phenyl-C$_{1-3}$alkoxy,
(e) phenyl,
(f) —CN,
(g) halo,
(h) —CONR$^9$R$^{10}$ wherein R$^9$ and R$^{10}$ are as defined above,
(i) —COR$^9$ wherein R$^9$ is as defined above,
(j) —CO$_2$R$^9$, wherein R$^9$ is as defined above;
(4) C$_{2-6}$alkynyl;
(5) phenyl, unsubstituted or substituted with one or more of the substituent(s) selected from:
(a) hydroxy,
(b) C$_{1-6}$alkoxy,
(c) C$_{1-6}$alkyl,
(d) C$_{2-5}$alkenyl,
(e) halo,
(f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above;
(o) —CO$_2$R$^9$, wherein R$^9$ is as defined above;
(6) halo,
(7) —CN,
(8) —CF$_3$,
(9) —NO$_2$,
(10) —SR$^{14}$, wherein R$^{14}$ is hydrogen or C$_{1-5}$alkyl,
(11) —SOR$^{14}$, wherein R$^{14}$ is as defined above,
(12) —SO$_2$R$^4$, wherein R$^{14}$ is as defined above,
(13) NR$^9$COR$^{10}$, wherein R$^9$ and R$^{10}$ are as defined above,
(14) CONR$^9$COR$^{10}$, wherein R$^9$ and R$^{10}$ are as defined above,
(15) NR$^9$R$^{10}$, wherein R$^9$ and R$^{10}$ are as defined above,
(16) NR$^9$CO$_2$R$^{10}$, wherein R$^9$ and R$^{10}$ are as defined above,
(17) hydroxy,
(18) C$_{1-6}$alkoxy,
(19) COR$^9$, wherein R$^9$ is as defined above,
(20) CO$_2$R$^9$, wherein R$^9$ is as defined above,
R$^{11}$, R$^{12}$ and R$^{13}$ are independently selected from the definitions of R$^6$, R$^7$ and R$^8$, or —OX;
Y is selected from the group consisting of:
(1) a single bond,
(2) —O—,
(3) —S—,
(4) —CO—,
(5) —CH$_2$—,
(6) —CHR$^{15}$—, and
(7) —CR$^{15}$R$^{16}$—, wherein R$^{15}$ and R$^{16}$ are independently selected from the group consisting of:
(a) C$_{1-6}$alkyl, unsubstituted or substituted with one or more of the substituents selected from:
(i) hydroxy,
(ii) oxo,
(iii) C$_{1-6}$alkoxy,
(iv) phenyl-C$_{1-3}$alkoxy,
(v) phenyl,
(vi) —CN,
(vii) halo,
(viii) —NR$^9$R$^{10}$, wherein R$^9$ and R$^{10}$ are as defined above,
(ix) —NR$^9$COR$^{10}$, wherein R$^9$ and R$^{10}$ are as defined above,
(x) —NR$^9$CO$_2$R$^{10}$, wherein R$^9$ and R$^{10}$ are as defined above,
(xi) —CONR$^9$R$^{10}$, wherein R$^9$ and R$^{10}$ are as defined above,
(xii) —COR$^9$, wherein R$^9$ is as defined above, and
(xiii) —CO$_2$R$^9$, wherein R$^9$ is as defined above;
(b) phenyl, unsubstituted or substituted with one or more of the substituent(s) selected from:
(i) hydroxy, (ii) $C_{1-6}$alkoxy,
(iii) $C_{1-6}$alkyl,
(iv) $C_{2-5}$alkenyl,
(v) halo,
(vi) —CN,
(vii) —NO$_2$,
(viii) —CF$_3$,
(ix) —(CH$_2$)$_m$—NR$^9$R$^{10}$, wherein m, R$^9$ and R$^{10}$ are as defined above,
(x) —NR$^9$COR$^{10}$, wherein R$^9$ and R$^{10}$ are as defined above,
(xi) —NR$^9$CO$_2$R$^{10}$, wherein R$^9$ and R$^{10}$ are as defined above,
(xii) —CONR$^9$R$^{10}$, wherein R$^9$ and R$^{10}$ are as defined above,
(xiii) —CO$_2$NR$^9$R$^{10}$, wherein R$^9$ and R$^{10}$ are as defined above,
(xiv) —COR$^9$, wherein R$^9$ is as defined above, and
(xv) —CO$_2$R$^9$, wherein R$^9$ is as defined above;
Z is selected from:
(1) hydrogen,
(2) $C_{1-4}$alkyl, and
(3) hydroxy, with the proviso that if Y is —O—, Z is other than hydroxy, or if Y is —CHR$^{15}$—, then Z and R$^{15}$ may be joined together to form a double bond.

Particularly preferred compounds of formula (I) are those wherein: R$^1$ is selected from the group consisting of:
(1) $C_{1-6}$alkyl, substituted with one or more of the substituents selected from:
  (a) heterocycle, wherein the heterocycle is selected from the group consisting of:
    (A) benzimidazolyl,
    (B) imidazolyl,
    (C) isoxazolyl,
    (D) isothiazolyl,
    (E) oxadiazolyl,
    (F) pyrazinyl,
    (G) pyrazolyl,
    (H) pyridyl,
    (I) pyrrolyl,
    (J) tetrazolyl,
    (K) thiadiazolyl,
    (L) triazolyl, and
    (M) piperidinyl,
and wherein the heterocycle is unsubstituted or substituted with one or more substituent(s) selected from:
  (i) $C_{1-6}$alkyl, unsubstituted or substituted with halo, —CF$_3$, —OCH$_3$, or phenyl,
  (ii) $C_{1-6}$alkoxy,
  (iii) oxo,
  (iv) thioxo,
  (v) cyano,
  (vi) —SCH$_3$,
  (vii) phenyl,
  (viii) hydroxy,
  (ix) trifluoromethyl,
  (x) —(CH$_2$)$_m$—NR$^9$R$^{10}$, wherein m is 0, 1 or 2, and R$^9$ and R$^{10}$ are independently selected from:
    (I) hydrogen,
    (II) $C_{1-6}$alkyl,
    (III) hydroxy$C_{1-6}$alkyl, and
    (IV) phenyl,
  (xi) —NR$^9$COR$^{10}$, wherein R$^9$ and R$^{10}$ are as defined above, and
  (xii) —CONR$^9$R$^{10}$, wherein R$^9$ and R$^{10}$ are as defined above, R$^2$ and R$^3$ are independently selected from the group consisting of:
(1) hydrogen;
(2) $C_{1-6}$alkyl
(3) $C_{2-6}$alkenyl, and
(5) phenyl; X is —O—;
R$^4$ is

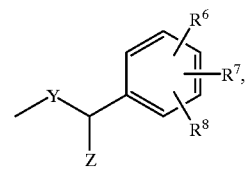

R$^5$ is phenyl, unsubstituted or substituted with halo;
R$^6$, R$^7$ and R$^8$ are independently selected from the group consisting of:
(1) hydrogen,
(2) $C_{1-6}$alkyl,
(3) halo, and
(4) —CF$_3$;
Y is —O—; and
Z is hydrogen or $C_{1-4}$alkyl;
and pharmaceutically acceptable salts thereof.

Particularly preferred compounds of formula (I) are:
4-(3-(1,2,4-triazolo)methyl)-2(S)-(3, 5-bis(trifluoromethyl)benzyloxy)-3(S)-phenyl-morpholine;
4-(3-(1,2,4-triazolo)methyl)-2(S)-(3,5-bis(trifluoromethyl)benzyloxy)-3(R)-phenyl-morpholine;
4-(3-(5-oxo-1H,4H-1,2,4-triazolo)methyl)-2(S)-(3,5-bis(trifluoromethyl)benzyloxy)-3(S)-phenyl-morpholine; and
2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; or a pharmaceutically acceptable salt thereof Further preferred NK-1 receptor antagonists are those described in International (PCT) Patent Specification No. WO 95/18124, i.e. compounds of formula (II):

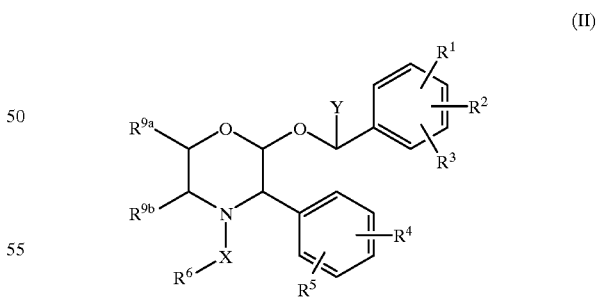

(II)

or a pharmaceutically acceptable salt or prodrug thereof, wherein

R$^1$ is hydrogen, halogen, $C_{1-6}$alkyl, $C_{1-6}$alkoxy, CF$_3$, NO$_2$, CN, SR$^a$, SOR$^a$, SO$_2$R$^a$, CO$_2$R$^a$, CONR$^a$R$^b$, $C_{2-6}$alkenyl, $C_{2-6}$alkynyl or $C_{1-4}$alkyl substituted by $C_{1-4}$alkoxy, where R$^a$ and R$^b$ each independently represent hydrogen or $C_{1-4}$alkyl;

R$^2$ is hydrogen, halogen, $C_{1-6}$alkyl, $C_{1-6}$alkoxy substituted by $C_{1-4}$alkoxy or CF$_3$;

$R^3$ is hydrogen, halogen or $CF_3$;

$R^4$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^5$ is hydrogen, halogen, $C_{1-6}$alkyl, $C_{1-6}$alkoxy substituted by $C_{1-4}$alkoxy or $CF_3$;

$R^6$ is a 5-membered or 6-membered heterocyclic ring containing 2 or 3 nitrogen atoms optionally substituted by =O, =S or a $C_{1-4}$alkyl group, and optionally substituted by a group of the formula $ZNR^7R^8$ where Z is $C_{1-6}$alkylene or $C_{3-6}$cycloalkylene;

$R^7$ is hydrogen, $C_{1-4}$alkyl, $C_{3-7}$cycloalkyl or $C_{3-7}$cycloalkyl$C_{1-4}$alkyl, or $C_{2-4}$alkyl substituted by $C_{1-4}$alkoxy or hydroxyl;

$R^8$ is hydrogen, $C_{1-4}$alkyl, $C_{3-7}$cycloalkyl or $C_{3-7}$cycloalkyl$C_{1-4}$alkyl, or $C_{2-4}$alkyl substituted by one or two substituents selected from $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by a hydroxy group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring of 4 to 7 ring atoms which may optionally contain an oxygen ring atom;

$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

X is an alkylene chain of 1 to 4 carbon atoms optionally substituted by oxo; and Y is a $C_{1-4}$alkyl group optionally substituted by a hydroxyl group;

with the proviso that if Y is $C_{1-4}$alkyl, $R^6$ is substituted at least by a group of formula $ZNR^7R^8$ as defined above.

Particularly preferred compounds of formula (II) are those of formula (IIa) and pharmaceutically acceptable salts thereof:

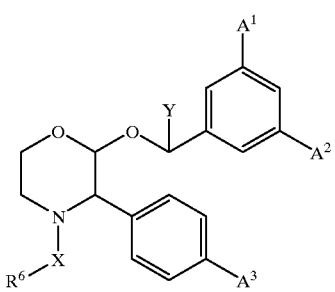

(IIa)

wherein:
$A^1$ is fluorine or $CF_3$;
$A^2$ is fluorine or $CF_3$;
$A^3$ is fluorine or hydrogen;
and X, Y and $R^6$ are as defined in relation to formula (II).

Particularly preferred compounds of formula (II) include:
2-(R)-(1-(R)-(3,5-bis(trifluoromethyl)phenyl)ethoxy)-4-(5-(dimethylamino) methyl-1,2,3-triazol-4-yl)methyl-3-(S)-phenylmorpholine;
2-(R)-(1-(R)-(3,5-bis(trifluoromethyl)phenyl)ethoxy)-4-(5-(dimethylamino) methyl-1,2,3-triazol-4-yl)methyl-3-(S)-(4-fluorophenyl)morpholine;
and pharmaceutically acceptable salts thereof.

Further preferred NK-1 receptor antagonists are those described in European Patent Specification No. WO 95/23798, i.e. compounds of formula (III):

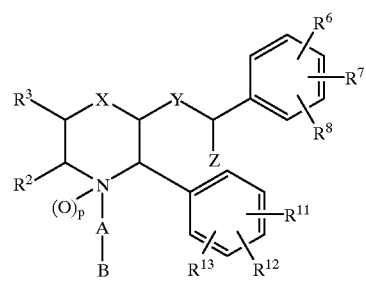

(III)

or a pharmaceutically acceptable salt thereof, wherein:
$R^2$ and $R^3$ are independently selected from the group consisting of:
(1) hydrogen,
(2) $C_{1-6}$alkyl, unsubstituted or substituted with one or more of the substituents selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$NR^9R^{10}$, wherein $R^9$ and $R^{10}$ are independently selected from:
    (i) hydrogen,
    (ii) $C_{1-6}$alkyl,
    (iii) hydroxy-$C_{1-6}$alkyl, and
    (iv) phenyl,
  (i) —$NR^9COR^{10}$, wherein $R^9$ and $R^{10}$ are as defined above,
  (j) —$NR^9CO_2R^{10}$, wherein $R^9$ and $R^{10}$ are as defined above,
  (k) —$CONR^9R^{10}$, wherein $R^9$ and $R^{10}$ are as defined above,
  (l) —$COR^9$, wherein $R^9$ is as defined above, and
  (m) —$CO_2R^9$, wherein $R^9$ is as defined above;
(3) $C_{2-6}$alkenyl, unsubstituted or substituted with one or more of the substituent(s) selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$CONR^9R^{10}$ wherein $R^9$ and $R^{10}$ are as defined above,
  (i) —$COR^9$ wherein $R^9$ is as defined above,
  (j) —$CO_2R^9$, wherein $R^9$ is as defined above;
(4) $C_{2-6}$alkynyl;
(5) phenyl, unsubstituted or substituted with one or more of the substituent(s) selected from:

(a) hydroxy,
(b) $C_{1-6}$alkoxy,
(c) $C_{1-6}$alkyl,
(d) $C_{2-5}$alkenyl,
(e) halo,
(f) —CN,
(g) —$NO_2$,
(h) —$CF_3$,
(i) —$(CH_2)_m NR^9 R^{10}$, wherein m, $R^9$ and $R^{10}$ are as defined above,
(j) —$NR^9 COR^{10}$, wherein $R^9$ and $R^{10}$ are as defined above,
(k) —$NR^9 CO_2 R^{10}$, wherein $R^9$ and $R^{10}$ are as defined above,
(l) —$CONR^9 R^{10}$, wherein $R^9$ and $R^{10}$ are as defined above,
(m) —$CO_2 NR^9 R^{10}$, wherein $R^9$ and $R^{10}$ are as defined above,
(n) —$COR^9$, wherein $R^9$ is as defined above,
(o) —$CO_2 R^9$, wherein $R^9$ is as defined above;
and the groups $R^2$ and $R^3$ may be joined together to form a carbocyclic ring selected from the group consisting of:
(a) cyclopentyl,
(b) cyclohexyl,
(c) phenyl,
and wherein the carbocyclic ring is unsubstituted or substituted with one or more substituents selected from:
(i) $C_{1-6}$alkyl,
(ii) $C_{1-6}$alkoxy,
(iii) —$NR^9 R^{10}$, wherein $R^9$ and $R^{10}$ are as defined above,
(iv) halo, and
(v) trifluoromethyl;
and the groups $R^2$ and $R^3$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl,
and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —$NR^9 R^{10}$, wherein $R^9$ and $R^{10}$ are as defined above,
(v) halo, and
(vi) trifluoromethyl;
$R^6$, $R^7$ and $R^8$ are independently selected from the group consisting of:
(1) hydrogen;
(2) $C_{1-6}$alkyl, unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9 R^{10}$, wherein $R^9$ and $R^{10}$ are as defined above,
(i) —$NR^9 COR^{10}$, wherein $R^9$ and $R^{10}$ are as defined above,
(j) —$NR^9 CO_2 R^{10}$, wherein $R^9$ and $R^{10}$ are as defined above,
(k) —$CONR^9 R^{10}$, wherein $R^9$ and $R^{10}$ are as defined above,
(l) —$COR^9$, wherein $R^9$ is as defined above, and
(m) —$CO_2 R^9$, wherein $R^9$ is as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9 R^{10}$ wherein $R^9$ and $R^{10}$ are as defined above,
(i) —$COR^9$ wherein $R^{10}$ is as defined above,
(j) —$CO_2 R^9$, wherein $R^9$ is as defined above;
(4) $C_{2-6}$alkynyl;
(5) phenyl, unsubstituted or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —$NO_2$,
(h) —$CF_3$,
(i) —$(CH_2)_m$—$NR^9 R^{10}$, wherein m, $R^9$ and $R^{10}$ are as defined above,
(j) —$NR^9 COR^{10}$, wherein $R^9$ and $R^{10}$ are as defined above,
(k) —$NR^9 CO_2 R^{10}$, wherein $R^9$ and $R^{10}$ are as defined above,
(l) —$CONR^9 R^{10}$, wherein $R^9$ and $R^{10}$ are as defined above,
(m) —$CO_2 NR^9 R^{10}$, wherein $R^9$ and $R^{10}$ are as defined above,
(n) —$COR^9$, wherein $R^9$ is as defined above,
(o) —$CO_2 R^9$, wherein $R^9$ is as defined above;
(6) halo,
(7) —ON,
(8) —$CF_3$,
(9) —$NO_2$,
(10) —$SR^{14}$, wherein $R^{14}$ is hydrogen or $C_{1-5}$alkyl,
(11) —$SOR^{14}$, wherein $R^{14}$ is as defined above,
(12) —$SO_2 R^{14}$, wherein $R^{14}$ is as defined above,
(13) $NR^9 COR^{10}$, wherein $R^9$ and $R^{10}$ are as defined above,
(14) $CONR^9 COR^{10}$, wherein $R^9$ and $R^{10}$ are as defined above,
(15) $NR^9 R^{10}$, wherein $R^9$ and $R^{10}$ are as defined above,
(16) $NR^9 CO_2 R^{10}$, wherein $R^9$ and $R^{10}$ are as defined above,
(17) hydroxy,
(18) $C_{1-6}$alkoxy,
(19) $COR^9$, wherein $R^9$ is as defined above,
(20) $CO_2 R^9$, wherein $R^9$ is as defined above,
(21) 2-pyridyl,
(22) 3-pyridyl,
(23) 4-pyridyl,
(24) 5-tetrazolyl,
(25) 2-oxazolyl, and
(26) 2-thiazolyl;
$R^{11}$, $R^{12}$ and $R^{13}$ are independently selected from the definitions of $R^6$, $R^7$ and $R^8$, or —OX;
A is selected from the group consisting of:

(1) $C_{1-6}$alkyl, unsubstituted or substituted with one or more of the substituents selected from:
   (a) hydroxy,
   (b) oxo,
   (c) $C_{1-6}$alkoxy,
   (d) phenyl-$C_{1-3}$alkoxy,
   (e) phenyl,
   (f) —CN,
   (g) halo, wherein halo is fluoro, chloro, bromo or iodo,
   (h) —$NR^9R^{10}$, wherein $R^9$ and $R^{10}$ are as defined above,
   (i) —$NR^9COR^{10}$, wherein $R^9$ and $R^{10}$ are as defined above,
   (j) —$NR^9CO_2R^{10}$, wherein $R^9$ and $R^{10}$ are as defined above,
   (k) —$CONR^9R^{10}$, wherein $R^9$ and $R^{10}$ are as defined above,
   (l) —$COR^9$, wherein $R^9$ is as defined above, and
   (m) —$CO_2R^9$, wherein $R^9$ is as defined above;
(2) $C_{2-6}$alkenyl, unsubstituted or substituted with one or more of the substituent(s) selected from:
   (a) hydroxy,
   (b) oxo,
   (c) $C_{1-6}$alkoxy,
   (d) phenyl-$C_{1-3}$alkoxy,
   (e) phenyl,
   (f) —CN,
   (g) halo,
   (h) —$CONR^9R^{10}$ wherein $R^9$ and $R^{10}$ are as defined above,
   (i) —$COR^9$ wherein $R^9$ is as defined above, and
   (j) —$CO_2R^9$, wherein $R^9$ is as defined above; and
(3) $C_{2-6}$alkynyl;
B is a heterocycle, wherein the heterocycle is selected from the group consisting of:

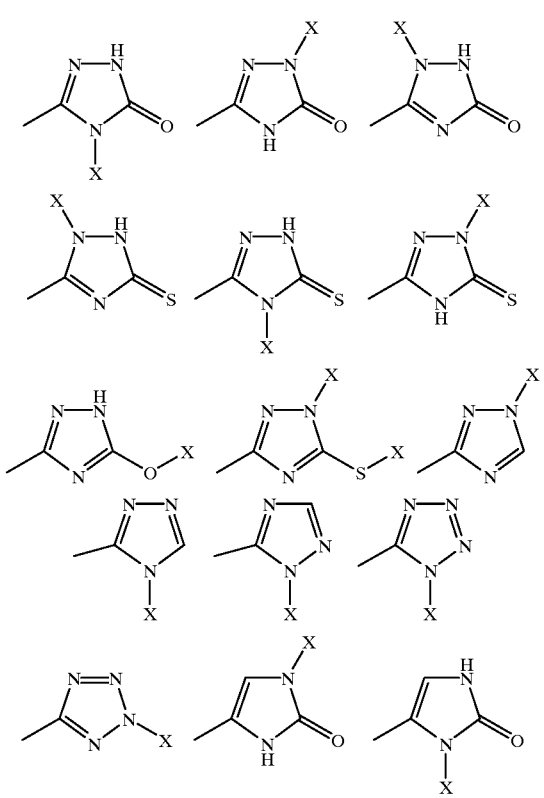

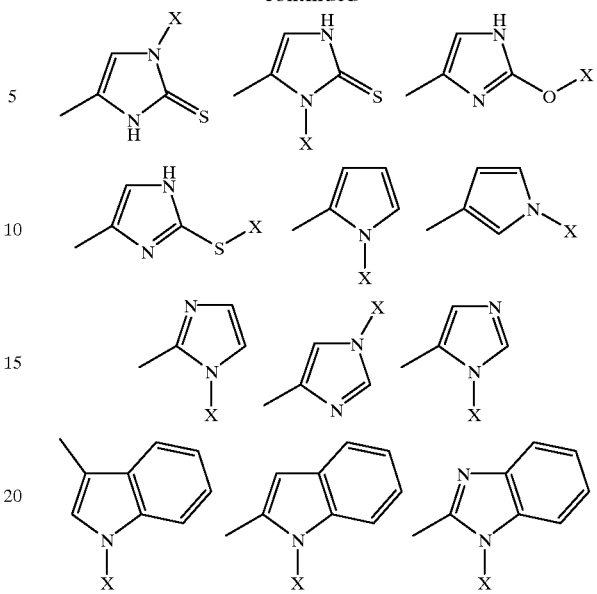

and wherein the heterocycle may be substituted in addition to -X with one or more substituent(s) selected from:
   (i) $C_{1-6}$alkyl, unsubstituted or substituted with halo, —$CF_3$, —$OCH_3$, or phenyl,
   (ii) $C_{1-6}$alkoxy,
   (iii) oxo,
   (iv) hydroxy,
   (v) thioxo,
   (vi) —$SR^9$, wherein $R^9$ is as defined above,
   (vii) halo,
   (viii) cyano,
   (ix) phenyl,
   (x) trifluoromethyl,
   (xi) —$(CH_2)_m$—$NR^9R^{10}$, wherein m is 0, 1 or 2, and $R^9$ and $R^{10}$ are as defined above,
   (xii) —$NR^9COR^{10}$, wherein $R^9$ and $R^{10}$ are as defined above,
   (xiii) —$CONR^9R^{10}$, wherein $R^9$ and $R^{10}$ are as defined above,
   (xiv) —$CO_2R^9$, wherein $R^9$ is as defined above, and
   (xv) —$(CH_2)_m$—$OR^9$, wherein m and $R^9$ are as defined above;
p is 0 or 1;
X is selected from:
   (a) —$PO(OH)O^-.M^+$, wherein $M^+$ is a pharmaceutically acceptable monovalent counterion,
   (b) —$PO(O^-)_2.2M^+$,
   (c) —$PO(O^-)_2.D^{2+}$, wherein $D^{2+}$ is a pharmaceutically acceptable divalent counterion,
   (d) —$CH(R^4)$—$PO(OH)O^-.M^+$, wherein $R^4$ is hydrogen or $C_{1-3}$alkyl,
   (e) —$CH(R^4)$—$PO(O^-)_2.2M^+$,
   (f) —$CH(R^4)$—$PO(O^-)_2.D^{2+}$,
   (g) —$SO_3^-.M^+$,
   (h) —$CH(R^4)$—$SO_3^-.M^+$,
   (i) —$CO$—$CH_2CH_2$—$CO_2^-.M^+$,
   (j) —$CH(CH_3)$—$O$—$CO$—$R^5$, wherein $R^5$ is selected from the group consisting of:

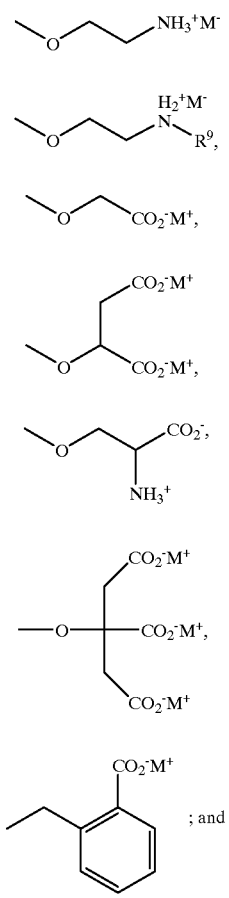

(k) hydrogen, with the proviso that if p is 0 and none of $R^{11}$, $R^{12}$ or $R^{13}$ are —OX, then X is other than hydrogen;
Y is selected from the group consisting of:
(1) a single bond,
(2) —O—,
(3) —S—,
(4) —CO—,
(5) —CH$_2$—,
(6) —CHR$^{15}$—, and
(7) —CR$^{15}$R$^{16}$—, wherein $R^{15}$ and $R^{16}$ are independently selected from the group consisting of:
(a) $C_{1-6}$alkyl, unsubstituted or substituted with one or more of the substituents selected from:
(i) hydroxy,
(ii) oxo,
(iii) $C_{1-6}$alkoxy,
(iv) phenyl-$C_{1-3}$alkoxy,
(v) phenyl,
(vi) —CN,
(vii) halo,
(viii) —NR$^9$R$^{10}$, wherein $R^9$ and $R^{10}$ are as defined above,
(ix) —NR$^9$COR$^{10}$, wherein $R^9$ and $R^{10}$ are as defined above,
(x) —NR$^9$CO$_2$R$^{10}$, wherein $R^9$ and $R^{10}$ are as defined above,
(xi) —CONR$^9$R$^{10}$, wherein $R^9$ and $R^{10}$ are as defined above, (xii) —COR$^9$, wherein $R^9$ is as defined above, and
(xiii) —CO$_2$R$^9$, wherein $R^9$ is as defined above;
(b) phenyl, unsubstituted or substituted with one or more of the substituent(s) selected from:
(i) hydroxy,
(ii) $C_{1-6}$alkoxy,
(iii) $C_{1-6}$alkyl,
(iv) $C_{2-5}$alkenyl,
(v) halo,
(vi) —CN,
(vii) —NO$_2$,
(viii) —CF$_3$,
(ix) —(CH$_2$)$_m$—NR$^9$R$^{10}$, wherein m, $R^9$ and $R^{10}$ are as defined above,
(x) —NR$^9$COR$^{10}$, wherein $R^9$ and $R^{10}$ are as defined above,
(xi) —NR$^9$CO$_2$R$^{10}$, wherein $R^9$ and $R^{10}$ are as defined above,
(xii) —CONR$^9$R$^{10}$, wherein $R^9$ and $R^{10}$ are as defined above,
(xiii) —CO$_2$NR$^9$R$^{10}$, wherein $R^9$ and $R^{10}$ are as defined above,
(xiv) —COR$^9$, wherein $R^9$ is as defined above, and
(xv) —CO$_2$R$^9$, wherein $R^9$ is as defined above;
Z is selected from:
(1) hydrogen,
(2) $C_{1-6}$alkyl, and
(3) hydroxy, with the proviso that if Y is —O—, Z is other than hydroxy, or if Y is —CHR$^{15}$—, then Z and $R^{15}$ may be joined together to form a double bond.
Particularly preferred compounds of formula (III) are those wherein:
$R^2$ and $R^3$ are independently selected from the group consisting of:
(1) hydrogen,
(2) $C_{1-6}$alkyl,
(3) $C_{2-6}$alkenyl, and
(4) phenyl;
$R^6$, $R^7$ and $R^8$ are independently selected from the group consisting of:
(1) hydrogen,
(2) $C_{1-6}$alkyl,
(3) fluoro,
(4) chloro,
(5) bromo,
(6) iodo, and
(7) —CF$_3$;
$R^{11}$, $R^{12}$ and $R^{13}$ are independently selected from the group consisting of:
(1) fluoro,
(2) chloro,
(3) bromo, and
(4) iodo;
A is unsubstituted $_{1-6}$alkyl;
B is selected from the group consisting of:

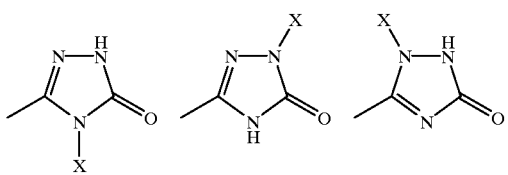

21
-continued

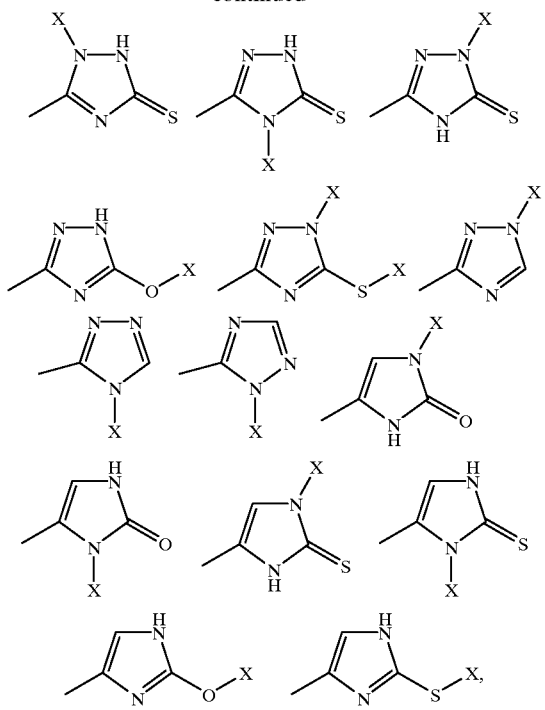

p is 0 or 1;

X is selected from:

(a) —PO(OH)O⁻.M⁺, wherein M⁺ is a pharmaceutically acceptable monovalent counterion, (b) —PO(O⁻)₂.2M⁺, (c) —PO(O⁻)₂.D²⁺, wherein D²⁺ is a pharmaceutically acceptable divalent counterion, (d) —CH(R⁴)—PO(OH)O⁻.M⁺, wherein R⁴ is hydrogen or $C_{1-3}$alkyl, (e) —CH(R⁴)—PO(O⁻)₂.2M⁺, (f) —CH(R⁴)—PO(O⁻)₂.D²⁺, (i) —CO—CH₂CH₂—CO₂⁻.M⁺, (j) —CH(CH₃)—O—CO—R⁵, wherein R⁵ is selected from the group consisting of:

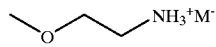 (i)

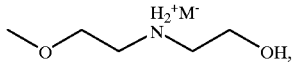 (ii)

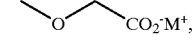 (iii)

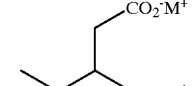 (iv)

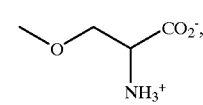 (v)

22
-continued

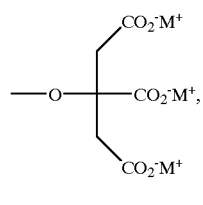 (vi)

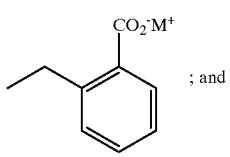 (vii)

Y is —O—;

Z is hydrogen or $C_{1-6}$alkyl;

and pharmaceutically acceptable salts thereof.

Particularly preferred compounds of formula (III) include:

(1) 2-(S)-(3,5-bis(trifluoromethyl)benzyloxy)-3-(S)-phenyl-4-(3-(5-oxo-1H,4H-1,2,4-triazolo)methyl)morpholine N-oxide;

(2) 2-(S)-(3,5-bis(trifluoromethyl)benzyloxy) 3-(S)-phenyl-4-(3-(4-(ethoxycarbonyloxy-1-ethyl)-5-oxo-1H-1,2,4-triazolo)methyl)morpholine;

(3) 2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;

(4) 2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

(5) 2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

(6) 2-(R)-(1-(R)-(3,5-bis(trifluoromethyl)phenyl)ethoxy)-3-(S)-(₄-fluorophenyl)-4-(3-(5-oxyphosphoryl-1H-1,2,4-triazolo)methyl)morpholine;

(7) 2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

and pharmaceutically acceptable salts thereof.

Further preferred NK-1 receptor antagonists are those described in European Patent Specification No. WO 96/05181, i.e. compounds of formula (IV):

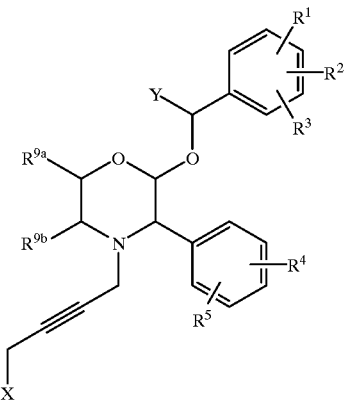 (IV)

wherein

X is a group of the formula NR⁶R⁷ or a C- or N-linked imidazolyl ring;

Y is hydrogen or $C_{1-4}$alkyl optionally substituted by a hydroxy group;

R¹ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

R² is hydrogen, halogen, $C_{1-6}$alkyl, $C_{1-6}$alkoxy substituted by $C_{1-4}$alkoxy or $CF_3$;

R³ is hydrogen, halogen or $CF_3$;

R⁴ is hydrogen, halogen, $C_{1-6}$alkyl, $C_{1-6}$alkoxy, hydroxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

R⁵ is hydrogen, halogen, $C_{1-6}$alkyl, $C_{1-6}$alkoxy substituted by $C_{1-4}$alkoxy or $CF_3$;

R⁶ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;

R⁷ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by one or two substituents selected from $C_{1-4}$alkoxy, hydroxy or a 4, 5 or 6 membered heteroaliphatic ring containing one or two heteroatoms selected from N, O and S;

or R⁶ and R⁷, together with the nitrogen atom to which they are attached, form a saturated or partially saturated heterocyclic ring of 4 to 7 ring atoms, which ring may optionally contain in the ring one oxygen or sulphur atom or a group selected from NR⁸, S(O) or $S(O)_2$ and which ring may be optionally substituted by one or two groups selected from hydroxy$C_{1-4}$alkyl, $C_{1-4}$alkoxy$C_{1-4}$alkyl, oxo, $COR^a$ or $CO_2R^a$ where $R^a$ is as previously defined;

or R⁶ and R⁷ together with the nitrogen atom to which they are attached, form a non-aromatic azabicyclic ring system of 6 to 12 ring atoms;

R⁸ is hydrogen, $C_{1-4}$alkyl, hydroxy$C_{1-4}$alkyl or $C_{1-4}$alkoxy$C_{1-4}$alkyl; and $R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

and pharmaceutically acceptable salts thereof

Particularly preferred compounds of formula (IV) are those of formula (IVa) and pharmaceutically acceptable salts thereof.

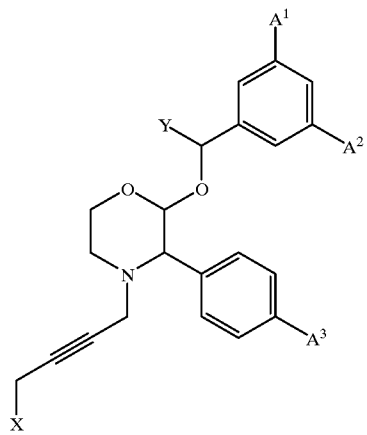

(IVa)

wherein
A¹ is fluorine or $CF_3$;
A² is fluorine or $CF_3$;
A³ is fluorine or hydrogen;
and X and Y are as defined in relation to formula (I).

Specific compounds of formula (IV) of use in the present invention include:

2-(R)-(1-(R)-(3,5-bis(trifluoromethyl)phenyl)ethoxy)-3-(S)-(4-fluorophenyl)-4-(4-morpholinobut-2-yn-yl) morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl) morpholine;

4-(4-azetidinylbut-2-yn-yl)-2-(R)-(1-(R)-(3,5-bis (trifluoromethyl)phenyl) ethoxy)-3-(S)-(4-fluorophenyl) morpholine;

2-(R)-(1-(R)-(3,5-bis(trifluoromethyl)phenyl)ethoxy)-3-(S)-(4-fluorophenyl)-4-(4-imidazolylbut-2-yn-yl) morpholine;

2-(R)-(1-(R)-(3,5-bis(trifluoromethyl)phenyl)ethoxy)-3-(S)-(4-fluorophenyl)-4-(4-(N-methylpiperazinyl)but-2-yn-yl)morpholine;

4-(4-bis(2-methoxyethyl)aminobut-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-pyrrolidinobut-2-yn-yl) morpholine;

3-(S)-(4-fluorophenyl)-2-(R)-(1-(R)-(3-fluoro-5-(trifluoromethyl)phenyl) ethoxy)-4-(4-morpholinobut-2-yn-yl)morpholine;

3-(S)-(4-fluorophenyl)-4-(4-morpholinobut-2-yn-yl)-2-(R)-(1-(R)-(3-(trifluoromethyl)phenyl)ethoxy)morpholine;

4-(4-azetidinylbut-2-yn-yl)-3-(S)-(4-fluorophenyl)-2-(R)-(1-(R)-(3-(trifluoromethyl)phenyl)ethoxy)morpholine;

2-(R)-(1-(R)-(3,5-bis(trifluoromethyl)phenyl)ethoxy)-4-(4-(N-(2-methoxyethyl)-N-methyl)aminobut-2-yn-yl)-3-(S)-phenylmorpholine;

2-(R)-(1-(R)-(3,5-bis(trifluoromethyl)phenyl)ethoxy)-4-(4-(N-cyclopropyl-N-(2-methoxyethyl)amino)but-2-yn-yl)-3-(S)-phenylmorpholine;

2-(R)-(1-(R)-(3,5-bis(trifluoromethyl)phenyl)ethoxy)-4-(4-(N-isopropyl-N-(2-methoxyethyl)amino)but-2-yn-yl)-3-(S)-phenylmorpholine;

4-(4-(N,N-dimethylamino)but-2-yn-yl)-3-(S)-(4-fluorophenyl)-2-(R)-(1-(S)-(3-fluoro-5-(trifluoromethyl) phenyl-2-hydroxyethoxy)morpholine;

4-(4-azetidinylbut-2yn-yl)-3-(S)-(4-fluorophenyl)-2-(R)-(1-(S)-(3-fluoro-5-(trifluoromethyl)phenyl)-2-hydroxyethoxy)morpholine;

2-(R)-(1-(S)-(3,5-bis(trifluoromethyl)phenyl)-2-hydroxyethoxy)-4-(4-(N,N-dimethylamino)but-2-yn-yl)-3-(S)-(4-fluorophenyl)morpholine;

4-(4-azetidinylbut-2-yn-yl)-2-(R)-(1-(S)-(3,5-bis(trifluoromethyl)phenyl-2-hydroxyethoxy)-3-(S)-(4-fluorophenyl)morpholine;

4-(4—N-bis(2-methoxy)ethyl-N-methylamino)but-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-(2-(S)-(methoxymethyl)pyrrolidino)but-2-yn-yl)morpholine;

4-(4-(7-azabicyclo[2.2.1]heptano)but-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-4-(4-diisopropylaminobut-2-yn-yl)-3-(S)-(4-fluorophenyl)morpholine;

2-(R)-(1-(R)-(3-fluoro-5-(trifluoromethyl)phenyl)ethoxy)-4-(4-(2-(S)-(methoxymethyl)pyrrolidino)but-2-yn-yl)-3-(S)-phenylmorpholine;

2-(R)-(1-(R)-(3,5-bis(trifluoromethyl)phenyl)ethoxy)-3-(S)-(4-fluorophenyl)-4-(4-(2-(S)-hydroxymethyl)pyrrolidino)but-2-yn-yl)morpholine;

and pharmaceutically acceptable salts thereof.

Another class of NK-1 receptor antagonists of use in the present invention is that described in European Patent Specification No. 0 436 334, i.e. compounds of formula (V):

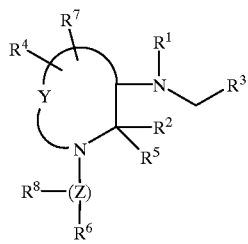

(V)

or a pharmaceutically acceptable salt thereof, wherein

Y is $(CH_2)_n$ wherein n is an integer from 1 to 4, and wherein any one of the carbon-carbon single bonds in said $(CH_2)_n$ may optionally be replaced by a carbon-carbon double bond, and wherein any one of the carbon atoms of said $(CH_2)_n$ may optionally be substituted with $R^4$, and wherein any one of the carbon atoms of said $(CH_2)_n$ may optionally be substituted with $R^7$;

Z is $(CH_2)_m$ wherein n is an integer from 0 to 6, and wherein any one of the carbon-carbon single bonds of $(CH_2)_m$ may optionally be replaced by a carbon-carbon double bond or a carbon-carbon triple bond, and any one of the carbon atoms of said $(CH_2)_m$ may optionally be substituted with $R^8$;

$R^1$ is hydrogen or $C_{1-8}$alkyl optionally substituted with hydroxy, $C_{1-4}$alkoxy or fluoro;

$R^2$ is a radical selected from hydrogen, $C_{1-6}$ straight or branched alkyl, $C_{3-7}$cycloalkyl wherein one of the $CH_2$ groups in said cycloalkyl may optionally be replaced by NH, oxygen or sulphur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$C_{2-6}$alkyl, benzhydryl and benzyl, wherein each of said aryl and heteroaryl groups and the phenyl moieties of said benzyl, phenyl-$C_{2-6}$alkyl and benzhydryl may optionally be substituted with one or more substituents independently selected from halo, nitro, $C_{1-6}$alkyl, $C_{1-6}$alkoxy, trifluoromethyl, amino, $C_{1-6}$alkylamino, $C_{1-6}$alkyl-O—CO, $C_{1-6}$alkyl-O—CO—$C_{1-6}$alkyl, $C_{1-6}$alkyl-CO—O, $C_{1-6}$alkyl-CO—$C_1$-alkyl-O—, $C_{1-6}$alkyl-CO, $C_{1-6}$alkyl-CO—$C_{1-6}$alkyl—, di-$C_{1-6}$alkylamino, —CONH—$C_{1-6}$alkyl, $C_{1-6}$alkyl-CO—NH—$C_{1-6}$alkyl, —NHCOH and —NHCO—$C_{1-6}$alkyl; and wherein one of the phenyl moieties of said benzhydryl may optionally be replaced by naphthyl, thienyl, furyl or pyridyl;

$R^5$ is hydrogen, phenyl or $C_{1-6}$alkyl;

or $R^2$ and $R^5$ together with the carbon to which they are attached, form a saturated ring having from 3 to 7 carbon atoms wherein one of the $CH_2$ groups in said ring may optionally be replaced by oxygen, NH or sulfur;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of the $(CH_2)$ groups in said cycloalkyl may optionally be replaced by NH, oxygen or sulphur;

wherein each of said aryl and heteroaryl groups may optionally be substituted with one or more substituents, and said $C_{3-7}$cycloalkyl may optionally be substituted with one or two substituents, each of said substituents being independently selected from halo, nitro, $C_{1-6}$alkyl, $C_{1-6}$alkoxy, trifluoromethyl, amino, $C_{1-6}$alkylamino, —CO—NH—$C_{1-6}$alkyl, $C_{1-6}$alkyl-CO—NH—$C_{1-6}$alkyl, —NHCOH and —NHCO—$C_{1-6}$alkyl;

$R^4$ and $R^7$ are each independently selected from hydroxy, halogen, halo, amino, oxo, cyano, methylene, hydroxymethyl, halomethyl, $C_{1-6}$alkylamino, di-$C_{1-6}$alkylamino, $C_{1-6}$alkoxy, $C_{1-6}$alkyl-O—CO, $C_{1-6}$alkyl-O—CO—$C_{1-6}$alkyl, $C_{1-6}$alkyl-CO—O, $C_{1-6}$alkyl-CO—$C_{1-6}$alkyl-O—, $C_{1-6}$alkyl-CO—, $C_{1-6}$alkyl-CO—$C_{1-6}$alkyl, and the radicals set forth in the definition of $R^2$;

$R^6$ is —NHCOR$^9$, —NHCH$_2$R$^9$, SO$_2$R$^8$ or one of the radicals set forth in any of the definitions of $R^2$, $R^4$ and $R^7$;

$R^8$ is oximino (=NOH) or one of the radicals set forth in any of the definitions of $R^2$, $R^4$ and $R^7$;

$R^9$ is $C_{1-6}$alkyl, hydrogen, phenyl or phenyl$C_{1-6}$alkyl;

with the proviso that (a) when m is 0, $R^8$ is absent, (b) when $R^4$, $R^6$, $R^7$ or $R^8$ is as defined in $R^2$, it cannot form together with the carbon to which it is attached, a ring with $R^5$, and (c) when $R^4$ and $R^7$ are attached to the same carbon atom, then either each of $R^4$ and $R^7$ is independently selected from hydrogen, fluoro and $C_{1-6}$alkyl, or $R^4$ and $R^7$, together with the carbon to which they are attached, for a $C_{3-6}$ saturated carbocyclic ring that forms a spiro compound with the nitrogen-containing ring to which they are attached.

A particularly preferred compound of formula (V) is (2S,3S)-cis-3-(2-methoxybenzylamino)-2-phenylpiperidine; or a pharmaceutically acceptable salt thereof.

Another class of NK-1 receptor antagonists of use in the present invention is that described in International Patent Specification No. WO 93/21155, i.e. compounds of formula (VI):

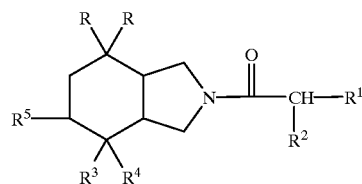

(VI)

or a pharmaceutically acceptable salt thereof, wherein radicals R are phenyl radicals optionally 2- or 3-substituted by a halogen atom or a methyl radical;

$R^1$ is optionally substituted phenyl, cyclohexadienyl, naphthyl, indenyl or optionally substituted heterocycle;

$R^2$ is H, halogen, OH, alkyl, aminoalkyl, alkylaminoalkyl, dialkylaminoalkyl, alkyloxy, alkylthio, acyloxy, carboxy, optionally substituted alkyloxycarbonyl, benzyloxycarbonyl, amino or acylamino;

$R^3$ is optionally 2-substituted phenyl;

$R^4$ is OH or fluorine when $R^5$ is H;

or $R^4$ and $R^5$ are OH;

or $R^4$ and $R^5$ together form a bond.

A particularly preferred compound of formula (VI) is (3aS, 4S, 7aS)-7,7-diphenyl-4-(2-methoxyphenyl)-2-[(2S)-(2-methoxyphenyl)propionyl] perhydroisoindol-4-ol; or a pharmaceutically acceptable salt thereof.

Another class of NK-1 receptor antagonists of use in the present invention is that described in European Patent Specification No. 0 591 040, i.e. compounds of formula (VII):

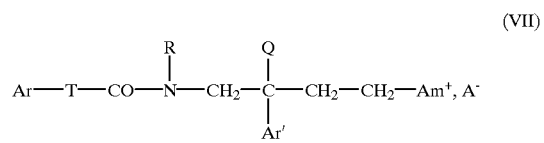

(VII)

wherein

Ar represents an optionally substituted mono-, di- or tricyclic aromatic or heteroaromatic group;

T represents a bond, a hydroxymethylene group, a $C_{1-4}$alkoxymethylene group or a $C_{1-5}$alkylene group;

Ar' represents a phenyl group which is unsubstituted or substituted by one or more substituents selected from halogen, preferably chlorine or fluorine, trifluoromethyl, $C_{1-4}$alkoxy, $C_{1-4}$alkyl where the said substituents may be the same or different; a thienyl group; a benzothienyl group; a naphthyl group; or an indolyl group;

R represents hydrogen, $C_{1-4}$alkyl, O—$C_{1-4}$alkoxy$C_{1-4}$alkyl, or $\omega$-$C_{2-4}$alkanoyloxy$C_{2-4}$alkyl;

Q represents hydrogen;

or Q and R together form a 1,2-ethylene, 1,3-propylene or 1,4-butylene group;

$Am^+$ represents the radical

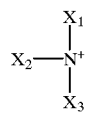

in which $X_1$, $X_2$ and $X_3$, together with the nitrogen atom to which they are attached, form an azabicyclic or azatricyclic ring system optionally substituted by a phenyl or benzyl group; and $A^-$ represents a pharmaceutically acceptable anion.

A particularly preferred compound of formula (VII) is (+)-1-[2-[3-(3,4-dichlorophenyl)-1-[(3-isopropoxyphenyl)acetyl]-3-piperidinyl]ethyl]-4-phenyl-1-azabicyclo[2,2,2]octane; or a pharmaceutically acceptable salt, especially the chloride, thereof.

Another class of NK-1 receptor antagonists of use in the present invention is that described in European Patent Specification No. 0 532 456, i.e. compounds of formula (VIII):

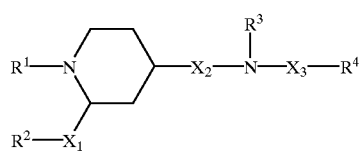

(VIII)

or a pharmaceutically acceptable salt thereof, wherein $R^1$ represents an optionally substituted aralkyl, aryloxyalykl, heteroaralkyl, aroyl, heteroaroyl, cycloalkylcarbonyl, aralkanoyl, heteroarylalkanoyl, aralkoxycarbonyl or arylcarbamoyl group or the acyl group of an $\alpha$-amino acid optionally N-substituted by a lower alkanoyl or carbamoyl-lower alkanoyl group;

$R^2$ represents cycloalkyl or an optionally substituted aryl or heteroaryl group;

$R^3$ represents hydrogen, alkyl, carbamoyl or an alkanoyl or alkenoyl group optionally substituted by carboxy or esterified or amidated carboxy;

$R^4$ represents an optionally substituted aryl group or an optionally partially saturated heteroaryl group;

$X_1$ represents methylene, ethylene, a bond, an optionally ketalised carbonyl group or an optionally etherified hydroxymethylene group;

$X_2$ represents alkylene, carbonyl or a bond; and $X_3$ represents carbonyl, oxo-lower alkyl, oxo(aza)-lower alkyl, or an alkyl group optionally substituted by phenyl, hydroxymethyl, optionally esterified or amidated carboxy, or (in other than the $\alpha$-position) hydroxy.

A particularly preferred compound of formula (VIII) is (2R*, 4S*)-2-benzyl-1-(3,5-dimethylbenzoyl)-N-(4-quinolinylmethyl)-4-piperidineamine; or a pharmaceutically acceptable salt thereof.

Another class of NK-1 receptor antagonists of use in the present invention is that described in European Patent Specification No. 0 443 132, i.e. compounds of formula (IX)

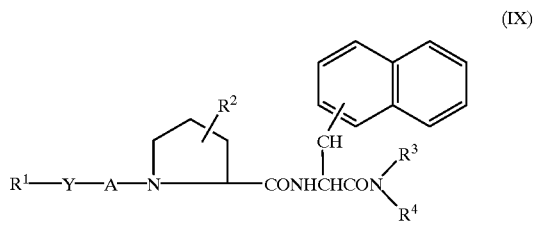

(IX)

or a pharmaceutically acceptable salt thereof, wherein $R^1$ is aryl, or a group of the formula:

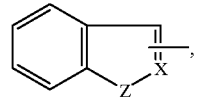

X is CH or N; and

Z is O or N—$R^5$, in which $R^5$ is hydrogen or lower alkyl;

$R^2$ is hydroxy or lower alkoxy;

$R^3$ is hydrogen or optionally substituted lower alkyl;

$R^4$ is optionally substituted ar(lower)alkyl;

A is carbonyl or sulfonyl; and

Y is a bond or lower alkenylene.

A particularly preferred compound of formula (IX) is the compound of formula (IXa)

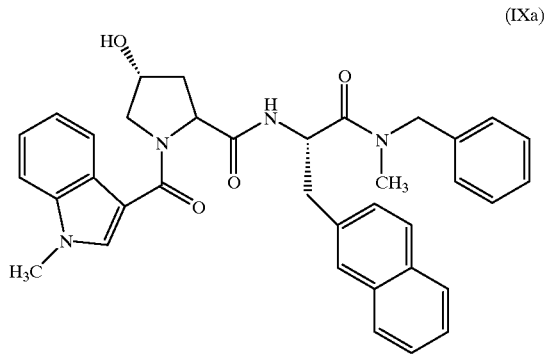

(IXa)

or a pharmaceutically acceptable salt thereof.

Another class of NK-1 receptor antagonists of use in the present invention is that described in International Patent Specification No. WO 92/17449, i.e. compounds of the formula (X)

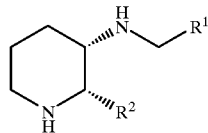

(X)

or a pharmaceutically acceptable salt thereof, wherein $R^1$ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said $C_{3-7}$cycloalkyl may optionally be substituted with one or two substituents, said substituents being independently selected from chloro, fluoro, bromo, iodo, nitro, $C_{1-10}$alkyl optionally substituted with from one to three fluoro groups, $C_{1-10}$alkoxy optionally substituted with from one to three fluoro groups, amino, $C_{1-10}$alkyl-S—, $C_{1-10}$alkyl-S(O)—, $C_{1-10}$alkyl-SO$_2$—, phenyl, phenoxy, $C_{1-10}$alkyl-SO$_2$NH—, $C_{1-10}$alkyl-SO$_2$NH—$C_{1-10}$akyl—, $C_{1-10}$alkylamino-di$C_{1-10}$alkyl—, cyano, hydroxy, cycloalkoxy having 3 to 7 carbon atoms, $C_{1-6}$alkylamino, $C_{1-6}$dialkylamino, HC(O)NH— and $C_{1-10}$alkyl-C(O)NH—; and $R^2$ is thienyl, benzhydryl, naphthyl or phenyl optionally substituted with from one to three substituents independently selected from chloro, bromo, fluoro, iodo, cycloalkoxy having 3 to 7 carbon atoms, $C_{1-10}$alkyl optionally substituted with from one to three fluoro groups and $C_{1-10}$alkoxy optionally substituted with from one to three fluoro groups.

A particularly preferred compound of formula (X) is (2S,3S)-3-(2-methoxy-5-trifluoromethoxybenzyl)-amino-2-phenylpiperidine; or a pharmaceutically acceptable salt thereof.

Another class of NK-1 receptor antagonists of use in the present invention is that described in International Patent Specification No. WO 95/08549, i.e. compounds of formula (XI)

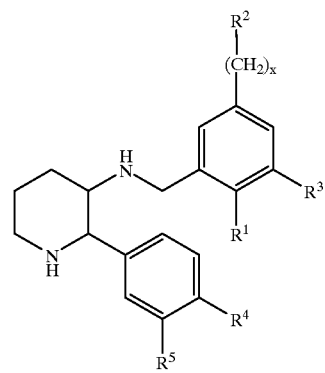

(XI)

or a pharmaceutically acceptable salt thereof, wherein
$R^1$ is a $C_{1-4}$alkoxy group;
$R^2$ is

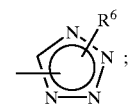

;

$R^3$ is a hydrogen or halogen atom;
$R^4$ and $R^5$ may each independently represent a hydrogen or halogen atom, or a $C_{1-4}$alkyl, $C_{1-4}$alkoxy or trifluoromethyl group;
$R^6$ is a hydrogen atom, a $C_{1-4}$alkyl, $(CH_2)_m$cyclopropyl, —S(O)$_n C_{1-4}$alkyl, phenyl, $NR^7R^8$, $CH_2C(O)CF_3$ or trifluoromethyl group;
$R^7$ and $R^8$ may each independently represent a hydrogen atom, or a $C_{1-4}$alkyl or acyl group;
x represents zero or 1;
n represents zero, 1 or 2; and
m represents zero or 1.

Particularly preferred compounds of formula (XI) are (2-methoxy-5-tetrazol-1-yl-benzyl)-([2S, 3S]-2-phenyl-piperidin-3-yl)-amine; and [2-methoxy-5-(5-trifluoromethyl-tetrazol-1-yl)-benzyl]-([2S,3S]-2-phenyl-piperidin-3-yl)-amine; or a pharmaceutically acceptable salt thereof.

Another class of tachykinin antagonists of use in the present invention is that described in International Patent Specification No. WO 95/14017, i.e. compounds of formula (XII)

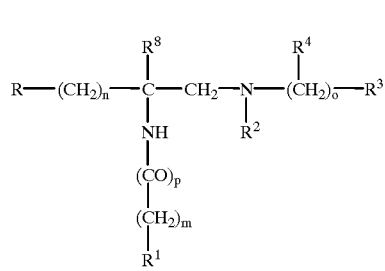

(XII)

or a pharmaceutically acceptable salt thereof, wherein
m is zero, 1, 2 or 3;
n is zero or 1;
o is zero, 1 or 2;
p is zero or 1;

R is phenyl, 2- or 3-indolyl, 2- or 3-indolinyl, benzothienyl, benzofuranyl, or naphthyl;

which R groups may be substituted with one or two halo, $C_{1-3}$alkoxy, trifluoromethyl, $C_{1-4}$alkyl, phenyl-$C_{1-3}$alkoxy, or $C_{1-4}$alkanoyl groups;

$R^1$ is trityl, phenyl, diphenylmethyl, phenoxy, phenylthio, piperazinyl, piperidinyl, pyrrolidinyl, morpholinyl, indolinyl, indolyl, benzothienyl, hexamethyleneiminyl, benzofuranyl, tetrahydropyridinyl, quinolinyl, isoquinolinyl, reduced quinolinyl, reduced isoquinolinyl, phenyl-($C_{1-4}$alkyl)—, phenyl-($C_{1-4}$alkoxy)—, quinolinyl-($C_{1-4}$alkyl)—, isoquinolinyl-($C_{1-4}$alkyl)—, reduced quniolinyl-($C_{1-4}$alkyl)—, reduced isoquinolinyl-($C_{1-4}$alkyl)—, benzoyl-($C_{1-3}$alkyl)—, $C_{1-4}$alkyl, or —NH—$CH_2$—$R^5$;

any one of which $R^1$ groups may be substituted with halo, $C_{1-4}$alkyl, $C_{1-4}$alkoxy, trifluoromethyl, amino, $C_{1-4}$alkylamino, di($C_{1-4}$alkyl)amino, or $C_{2-4}$alkanoylamino;

or any one of which $R^1$ groups may be substituted with phenyl, piperazinyl, $C_{3-8}$-cycloalkyl, benzyl, $C_{1-4}$alkyl, piperidinyl, pyridinyl, pyrimidinyl, $C_{2-6}$-alkanoylamino, pyrrolidinyl, $C_{2-6}$alkanoyl, or $C_{1-4}$alkoxycarbonyl;

any one of which groups may be substituted with halo, $C_{1-4}$alkyl, $C_{1-4}$alkoxy, trifluoromethyl, amino, $C_{1-4}$alkylamino, di($C_{1-4}$alkyl)amino, or $C_{2-4}$alkanoylamino;

or $R^1$ is amino, a leaving group, hydrogen, $C_{1-4}$alkylamino, or di($C_{1-4}$alkyl)amino;

$R^5$ is pyridyl, anilino-($C_{1-3}$alkyl)—, or anilinocarbonyl;

$R^2$ is hydrogen, $C_{1-4}$alkyl, $C_{1-4}$alkylsulfonyl, carboxy-($C_{1-3}$alkyl)—, $C_{1-3}$alkoxycarbonyl-($C_{1-3}$alkyl)—, or —CO—$R^6$;

$R^6$ is hydrogen, $C_{1-4}$alkyl, $C_{1-3}$haloalkyl, phenyl, $C_{1-3}$alkoxy, $C_{1-3}$hydroxyalkyl, amino, $C_{1-4}$alkylamino, di($C_{1-4}$alkyl)amino, or —$(CH_2)_q$-$R^7$;

q is zero to 3;

$R^7$ is carboxy, $C_{1-4}$alkoxycarbonyl, $C_{1-4}$alkylcarbonyloxy, amino, $C_{1-4}$alkylamino, di($C_{1-4}$alkyl)amino, $C_{1-6}$alkoxycarbonylamino, or phenoxy, phenylthio, piperazinyl, piperidinyl, pyrrolidinyl, morpholinyl, indolinyl, indolyl, benzothienyl, benzofuranyl, quinolinyl, phenyl-($C_{1-4}$alkyl)—, quinolinyl-($C_{1-4}$alkyl)—, isoquinolinyl-($C_{1-4}$alkyl)—, reduced quinolinyl-($C_{1-4}$alkyl)—, reduced isoquinolinyl-($C_{1-4}$alkyl)—, benzoyl-$C_{1-3}$alkyl any one of which aryl or heterocyclic $R^7$ groups may be substituted with halo, trifluoromethyl, $C_{1-4}$alkoxy, $C_{1-4}$alkyl, amino, $C_{1-4}$alkylamino, di($C_{1-4}$alkyl)amino, or $C_{2-4}$alkanoylamino;

or any one of which $R^7$ groups may be substituted with phenyl, piperazinyl, $C_{3-8}$cycloalkyl, benzyl, piperidinyl, pyridinyl, pyrimidinyl, pyrrolidinyl, $C_{2-6}$alkanoyl, or $C_{1-4}$alkoxycarbonyl;

any of which groups may be substituted with halo, trifluoromethyl, amino, $C_{1-4}$alkoxy, $C_{1-4}$alkyl, $C_{1-4}$alkylamino, di($C_{1-4}$alkyl)amino, or $C_{2-4}$alkanoylamino;

$R^8$ is hydrogen or $C_{1-6}$alkyl;

$R^3$ is phenyl, phenyl-($C_{1-6}$alkyl)—, $C_{3-8}$cycloalkyl, $C_{5-8}$cycloalkenyl, $C_{1-8}$alkyl, naphthyl, $C_{2-8}$alkenyl, or hydrogen;

any one or which groups except hydrogen may be substituted with one or two halo, $C_{1-3}$alkoxy, $C_{1-3}$alkylthio, nitro, trifluoromethyl, or $C_{1-3}$alkyl groups; and $R^4$ is hydrogen or $C_{1-3}$alkyl;

with the proviso that if $R^1$ is hydrogen or halo, $R^3$ is phenyl, phenyl-($C_{1-6}$alkyl)—, $C_{3-8}$cycloalkyl, $C_{5-8}$cycloalkenyl, or naphthyl.

A particularly preferred compound of formula (XII) is [N-(2-methoxybenzyl)acetylamino]-3-(1H-indol-3-yl)-2-[N-(2-(4-piperidin-1-yl)piperidin-1l-yl)acetylamino] propane; or a pharmaceutically acceptable salt thereof.

The preferred compounds of formulae (I), (II), (III) and (IV) will have the 2- and 3-substituents on the morpholine ring in the cis arrangement, the preferred stereochemistry being as shown in the following general formula:

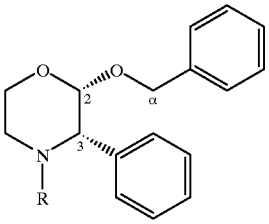

Where the benzyloxy moiety is α-substituted, the preferred stereochemistry of the α-carbon is either (R) when the substituent is an alkyl (e.g. methyl) group or (S) when the substituent is a hydroxyalkyl (e.g. hydroxymethyl) group.

Unless otherwise defined herein, suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl, n-butyl, sec-butyl and tert-butyl.

Unless otherwise defined herein, suitable alkenyl groups include straight-chained and branched alkenyl groups containing from 2 to 6 carbon atoms. Typical examples include vinyl and alkyl groups.

Unless otherwise defined herein, suitable alkynyl groups include straight-chained and branched alkynyl groups containing from 2 to 6 carbon atoms. Typical examples include ethynyl and propargyl groups.

Unless otherwise defined herein, suitable cycloalkyl groups include groups containing from 3 to 7 carbon atoms. Particular cycloalkyl groups are cyclopropyl and cyclohexyl.

Unless otherwise defined herein, suitable aryl groups include phenyl and naphthyl groups.

A particular aryl-$C_{1-6}$alkyl, e.g. phenyl-$C_{1-6}$alkyl, group is benzyl.

Unless otherwise defined herein, suitable heteroaryl groups include pyridyl, quinolyl, isoquinolyl, pyridazinyl, pyrimidinyl, pyrazinyl, pyranyl, furyl, benzofuryl, thienyl, benzthienyl, imidazolyl, oxadiazolyl and thiadiazolyl groups.

The term "halogen" as used herein includes fluorine, chlorine, bromine and iodine.

The compounds of use in this invention may have one or more asymmetric centres and can therefore exist as enantiomers and possibly as diastereoisomers. It is to be understood that the present invention relates to the use of all such isomers and mixtures thereof.

Suitable pharmaceutically acceptable salts of the NK-1 receptor antagonists of use in the present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, phosphoric acid or sulphuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

Suitable pharmaceutically acceptable salts of the SSRI of use in the present invention include those salts described above in relation to the salts of NK-1 receptor antagonists.

The present invention accordingly provides the use of a NK-1 receptor antagonist selected from the compounds of formulae (I), (II), (III), (IV), (V), (VI), (VII), (VIII), (IX), (X), (XI) and (XII) and an SSRI for the manufacture of a medicament for the treatment or prevention of obesity.

The present invention also provides a method for the treatment or prevention of obesity, which method comprises administration to a patient in need of such treatment an amount of a NK-1 receptor antagonist selected from the compounds of formulae (I), (II), (III), (IV), (V), (VI), (VII), (VIII), (IX), (X), (XI) and (XII) and an amount of an SSRI such that together they give effective relief.

In a further aspect of the present invention, there is provided a pharmaceutical composition for the treatment or prevention of obesity comprising a NK-1 receptor antagonist selected from the compounds of formulae (I), (II), (III), (IV), (V), (VI), (VII), (VIII), (IX), (X), (XI) and (XII) and an SSRI together with at least one pharmaceutically acceptable carrier or excipient.

It will be appreciated that the NK-1 receptor antagonist selected from the compounds of formulae (I), (II), (III), (IV), (V), (VI), (VII), (VIII), (IX), (X), (XI) and (XII) and an SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a NK-1 receptor antagonist selected from the compounds of formulae (I), (II), (III), (IV), (V), (VI), (VII), (VIII), (IX), (X), (XI) and (XII) and an SSRI as a combined-preparation for simultaneous, separate or sequential use in the treatment or prevention of obesity.

In a preferred aspect, the present invention accordingly provides the use of a NK-1 receptor antagonist selected from the compounds of formulae (I), (II), (III), (IV), (V), (VI), (VII), (VIII), (IX), (X), (XI) and (XII) and an SSRI selected from the group consisting of: fluoxetine, fluvoxamine, paroxetine and sertraline, for the manufacture of a medicament for the treatment or prevention of obesity.

The present invention also provides a method for the treatment or prevention of obesity, which method comprises administration to a patient in need of such treatment an amount of a NK-1 receptor antagonist selected from the compounds of formulae (I), (II), (III), (IV), (V), (VI), (VII), (VIII), (IX), (X), (XI) and (XII) and an SSRI selected from the group consisting of: fluoxetine, fluvoxamine, paroxetine and sertraline, such that together they give effective relief.

In a further aspect of the present invention, there is provided a pharmaceutical composition for the treatment or prevention of obesity comprising a NK-1 receptor antagonist selected from the compounds of formulae (I), (II), (III), (IV), (V), (VI), (VII), (VIII), (IX), (X), (XI) and (XII) and an SSRI selected from the group consisting of: fluoxetine, fluvoxamine, paroxetine and sertraline, together with at least one pharmaceutically acceptable carrier or excipient.

In a further or alternative aspect of the present invention, there is provided a product comprising a NK-1 receptor antagonist selected from the compounds of formulae (I), (II), (III), (IV), (V), (VI), (VII), (VIII), (IX), (X), (XI) and (XII) and an SSRI selected from the group consisting of: fluoxetine, fluvoxamine, paroxetine and sertraline, as a combined preparation for simultaneous, separate or sequential use in the treatment or prevention of obesity.

A particularly preferred SSRI is fluoxetine. Thus in a further preferred aspect, the present invention accordingly provides the use of a NK-1 receptor antagonist selected from the compounds of formulae (I), (II), (III), (IV), (V), (VI), (VII), (VIII), (IX), (X), (XI) and (XII) and fluoxetine, for the manufacture of a medicament for the treatment or prevention of obesity.

The present invention also provides a method for the treatment or prevention of obesity, which method comprises administration to a patient in need of such treatment an amount of a NK-1 receptor antagonist selected from the compounds of formulae (I), (II), (III), (IV), (V), (VI), (VII), (VIII), (IX), (X), (XI) and (XII) and an amount of fluoxetine, such that together they give effective relief.

In a further aspect of the present invention, there is provided a pharmaceutical composition for the treatment or prevention of obesity comprising a NK-1 receptor antagonist selected from the compounds of formulae (I), (II), (III), (IV), (V), (VI), (VII), (VIII), (IX), (X), (XI) and (XII) and fluoxetine, together with at least one pharmaceutically acceptable carrier or excipient.

In a further or alternative aspect of the present invention, there is provided a product comprising a NK-1 receptor antagonist selected from the compounds of formulae (I), (II), (III), (IV), (V), (VI), (VII), (VIII), (IX), (X), (XI) and (XII) and fluoxetine as a combined preparation for simultaneous, separate or sequential use in the treatment or prevention of obesity.

As stated above, the NK-1 receptor antagonist and the SSRI may be formulated in a single pharmaceutical composition or alternatively in individual pharmaceutical compositions for simultaneous, separate or sequential use in accordance with the present invention.

Preferably the compositions according to the present invention are in unit dosage forms such as tablets, pills, capsules, powders, granules, solutions or suspensions, or suppositories, for oral, parenteral or rectal administration, by inhalation or insufflation or administration by transdermal patches or by buccal cavity absorption wafers. Oral dosage forms are particularly preferred (e.g. tablets, capsules, pills and wafers).

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Preferred compositions for administration by injection include those comprising a NK-1 receptor antagonist as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Particularly preferred emulsion compositions are those prepared by mixing a NK-1 receptor antagonist selected from the compounds of formulae (I), (II), (III), (IV), (V), (VI), (VII), (VIII), (IX), (X), (XI) and (XII) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

The present invention further provides a process for the preparation of a pharmaceutical composition comprising a NK-1 receptor antagonist and an SSRI, which process comprises bringing a NK-1 receptor antagonist and an SSRI, into association with a pharmaceutically acceptable carrier or excipient.

When administered in combination, either as a single or as separate pharmaceutical composition(s), the NK-1 receptor antagonist and an SSRI, are presented in a ratio which is consistent with the manifestation of the desired effect. In particular, the ratio by weight of the NK-1 receptor antagonist and the SSRI will suitably be between 0.001 to 1 and 1000 to 1, and especially between 0.01 to 1 and 100 to 1.

A suitable dosage level for the NK-1 receptor antagonist about 0.05 to 1500 mg per day, preferably about 0.25 to 1500 mg per day, and especially about 0.25 to 500 mg/kg per day. The compounds may be administered on a regimen of up to 6 times per day, preferably 1 to 4 times per day, especially 1 or 2 times daily.

A suitable dosage level for the SSRI is about 0.5 to 1500 mg per day, preferably about 2.5 to 1000 mg per day, and especially about 2.5 to 500 mg per day. The compounds may be administered on a regimen of up to 6 times per day, preferably 1 to 4 times per day, especially 1 or 2 times daily.

It will be appreciated that the amount of the NK-1 receptor antagonist and the SSRI required for use in the treatment or prevention of obesity will vary not only with the particular compounds or compositions selected but also with the route of administration, the nature of the condition being treated, and the age and condition of the patient, and will ultimately be at the discretion of the patient's physician or pharmacist.

The compounds of formulae (I), (II), (III), (IV), (V), (VI), (VII), (VIII), (IX), (X), (XI) and (XII) may be prepared by the methods described in EP-A-0 577 394 (or WO 95/16679), WO 95/18124, WO 95/23798, WO 96/05181, EP-A-0 436 334, WO 93/21155, EP-A-0 591 040, EP-A-0 532 456, EP-A-0 443 132, WO 92/17449, WO 95/08549 and WO 95/14017, respectively.

Particularly preferred NK-1 receptor antagonists of the formulae (I), (II), (III), (IV), (V), (VI), (VII), (VIII), (IX), (X), (XI) and (XII) for use in the present invention are compounds which are potent. NK-1 receptor antagonists, i.e. compounds with an NK-1 receptor affinity ($IC_{50}$) of less than 100 nM.

Even more preferred NK-1 receptor antagonists of use in the present invention are compounds which are potent NK-1 receptor antagonists with an NK-1 receptor affinity ($IC_{50}$) of less than 10 nM, favourably less than 2 nM and preferably less than 1 nM.

Especially preferred NK-1 receptor antagonists of use in the present invention are orally active, long acting, CNS-penetrant NK-1 receptor antagonists, identified using a combination of the following assays:

ASSAY 1: NK-1 Receptor Binding

NK-1 receptor binding assays are performed in intact Chinese hamster ovary (CHO) cells expressing the human NK-1 receptor using a modification of the assay conditions described by Cascieri et al, *J. Pharmacol. Exp. Ther.*, 1992, 42, 458. Typically, the receptor is expressed at a level of $3 \times 10^5$ receptors per cell. Cells are grown in monolayer culture, detached from the plate with enzyme-free dissociation solution (Speciality Media Inc.), and washed prior to use in the assay. $^{125}$I-Tyr$^8$- substance P (0.1 nM, 2000 Ci/mmol; New England Nuclear) is incubated in the presence or absence of test compounds (dissolved in 5 µl dimethylsulphoxide, DMSO) with $5 \times 10^4$ CHO cells. Ligand binding is performed in 0.25 ml of 50M Tris-HCl, pH7.5, containing 5 mM MnCl$_2$, 150 mM NaCl, 0.02% bovine serum albumin (Sigma), 50 µg/ml chymostatin (Peninsula), 0.1 nM phenylmethylsulphonyl fluoride, 2 µg/ml pepstatin, 2 µg/ml leupeptin and 2.8 µg/ml furoyl saccharine. The incubation proceeds at room temperature until equilibrium is achieved (>40 minutes) and the receptor-ligand complex is harvested by filtration over GF/C filters pre-soaked in 0.1% polyethylenimine using a Tomtek 96-well harvester. Non-specific binding is determined using excess substance P (1 µM) and represents <10% of total binding.

ASSAY 2: Gerbil Foot-Tapping

CNS-penetrant NK-1 receptor antagonists for use in the present invention can be identified by their ability to inhibit foot tapping in gerbils induced by anxiogenic agents (such as pentagastrin) or central infusion of NK-1 receptor agonists such as GR73632, or caused by aversive stimulation such as foot shock or single housing, based on the method of Rupniak & Williams, *Eur. J. Pharmacol.,* 1994, 265, 179.

Male or female Mongolian gerbils (35–70 g) are anaesthetised by inhalation of an isoflurane/oxygen mixture to permit exposure of the jugular vein in order to permit administration of test compounds or vehicle in an injection volume of approximately 5 ml/kg i.v. Alternatively, test compounds may be administered orally or by subcutaneous or intraperitoneal routes. A skin incision is then made in the midline of the scalp to expose the skull. An anxiogenic agent (e.g. pentagastrin) or a selective NK-1 receptor agonist (e.g. GR73632 (d Ala[L-Pro$^9$,Me-Leu$^{10}$]-substance P-(7–11)) is infused directly into the cerebral ventricles (e.g. 3 pmol in 5 µl i.c.v., depending on test substance) by vertical insertion of a cuffed 27 gauge needle to a depth of 4.5 mm below bregma. The scalp incision is closed and the animal allowed to recover from anaesthesia in a clear perspex observation box (approximately 25 cm×20 cm×20 cm). The duration and/or intensity of hind foot tapping is then recorded continuously for approximately 5 minutes. Alternatively, the ability of test compounds to inhibit foot tapping evoked by aversive stimulation, such as foot shock or single housing, may be studied using a similar method of quantification.

ASSAY 3: Ferret Emesis

Individually housed male ferrets (1.0–2.5 kg) are dosed orally by gavage with test compound. Ten minutes later they are fed with approximately 100 g of tinned cat food. At 60 minutes following oral dosing, cisplatin (10 mg/kg) is given i.v. via a jugular vein catheter inserted under a brief period of halothane anaesthesia. The catheter is then removed, the jugular vein ligated and the skin incision closed. The ferrets recover rapidly from the anaesthetic and are mobile within 10–20 minutes. The animals are observed continuously during recovery from the anaesthetic and for 4 hours following the cisplatin injection, after which time the animals are killed humanely. The numbers of retches and vomits occurring during the 4 hours after cisplatin administration are recorded by trained observers.

ASSAY 4: Separation-Induced Vocalisation

Male and female guinea-pigs pups are housed in family groups with their mothers and littermates throughout the study. Experiments are commenced after weaning when the pups are at least 2 weeks old. Before entering an experiment, the pups may be screened to ensure that a vigorous vocalisation response is reproducibly elicited following maternal separation. The pups are placed individually in an observation cage (approximately 55 cm×39 cm×19 cm) in a room physically isolated from the home cage for approximately 15 minutes and the duration and/or number of vocalisation during this baseline period is recorded. Those animals which vocalise for longer than 5 minutes are employed for drug challenge studies (approximately 50% of available pups may fail to reach this criterion). On test days each pup receives an oral dose or an s.c. or i.p. injection of test compound or vehicle and is then immediately returned to the home cage with its mother and siblings for at least 30 to 60 minutes (or for up to 4 hours following an oral dose, dependent upon the oral pharmacokinetics of the test compound) before social isolation for 15 minutes as described above. The duration and/or number of vocalisation on drug treatment days may be expressed as a percentage of the pre-treatment baseline value for each animal or compared with values obtained in vehicle-treated animals. The same subjects may be retested once weekly for up to 6 weeks. Between 6 and 8 animals receive each test compound at each dose tested.

A suitable selection cascade for NK$_1$ antagonists of use according to the present invention is as follows:

(i) Determine affinity for human NK$_1$ receptor in radioligand binding studies (Assay 1); select compounds with IC$_{50} \leq 10$ nM, preferably IC$_{50} \leq 2$ nM, especially IC$_{50}$>1 nM.

(ii) Determine ability of compounds to penetrate CNS by their ability to inhibit foot tapping in gerbils induced by central injection of an NK$_1$ agonist (Assay 2); select compounds that inhibit foot tapping with ID$_{50} \leq 3$ mg/kg i.v., and preferably ID$_{50} \leq 1$ mg/kg i.v. when administered immediately prior to central NK$_1$ agonist challenge, or ID$_{50} \leq 30$ mg/kg p.o., and preferably ID$_{50} \leq 10$ mg/kg p.o. 1 hour prior to challenge.

(iii) Determine central duration of action of compounds in gerbil foot tapping assay following intravenous administration 24 hours prior to central NK$_1$ agonist challenge; select compounds showing $\leq 25$-fold loss of potency compared with ID$_{50}$ determined in step (ii) above with the proviso that ID$_{50} \leq 10$ mg/kg i.v., and preferably $\leq 5$ mg/kg i.v. after 24 hour pretreatment.

(iv) Determine oral bioavailability of compounds by pharmacokinetic analysis, activity in gerbil foot tapping assay following oral administration and/or by ability to inhibit cisplatin-induced emesis in ferrets (Assay 3); select compounds with ID$_{90} \leq 3$ mg/kg p.o., and preferably ID$_{90} \leq 1$mg/kg p.o.

Particularly preferred compounds of use in the present invention are identified using steps (i) to (iv) followed by step (v):

(v) Determine activity of compounds in assays sensitive to conventional serotonergic drugs (inhibition of pharmacologically evoked foot tapping in gerbils and/or inhibition of distress vocalisations in guinea-pig pups (Assay 4)). Select compounds with ID$_{50} \leq 20$ mg/kg, and preferably ID$_{50} \leq 10$ mg/kg.

Yet further preferred compounds of use in the present invention may be selected from those compounds which satisfy the NK-1 receptor binding criteria of step (i) which, in addition, have $\leq 5$-fold shift in affinity when incubated in the presence of human serum albumin (HSA) to show non-specific protein binding.

One example of a NK-1 receptor antagonist of use in the present invention is the compound 2-(R)-(1-(R)-(3,5-bis (trifluoromethyl)phenyl)-ethoxy)-3-(S)-(4-fluorophenyl)-4-(3-(5-oxo-1H,4H-1,2,4-triazolo)methyl)-morpholine, the preparation of which is described in International Patent Specification No. WO 95/16679. In the aforementioned assays, this compound has the following activity:

| | |
|---|---|
| human NK-1 receptor binding | $IC_{50} = 0.1$ nM |
| gerbil foot-tapping (5 mins.) | $ID_{50} = 0.36$ mg/kg i.v. |
| gerbil foot-tapping (24 hrs.) | $ID_{50} = 0.33$ mg/kg i.v. |
| ferret emesis | $ID_{90} < 3$ mg/kg p.o. |
| guinea-pig vocalisation (4 hrs. pretreatment) | $ID_{50} = 0.73$ mg/kg p.o. |

Another example of a NK-1 receptor antagonist of use in the present invention is the compound 2-(R)-(1-(R)-(3,5-bis (trifluoromethyl)phenyl)ethoxy)-4-(5-(N,N-dimethylamino) methyl-1,2,3-triazol-4-yl)methyl-3-(S)-phenylmorpholine, the preparation of which is described in International Patent Specification No. WO 95/18124. In the aforementioned assays, this compound has the following activity:

| | |
|---|---|
| human NK-1 receptor binding | $IC_{50} = 0.25$ nM |
| gerbil foot-tapping (5 mins.) | $ID_{50} = 0.12$ mg/kg i.v. |
| gerbil foot-tapping (24 hrs.) | $ID_{50} = 0.17$ mg/kg i.v. |
| guinea-pig vocalisation | $ID_{50} = 0.5$ mg/kg s.c. |

Assay 4, which involves the inhibition of separation-induced vocalisations in guinea-pig pups, has been used to demonstrate the potentiation of the effects of fluoxetine when co-administered with a CNS-penetrant NK-1 antagonist.

Test Compound A is 2-(R)-(1-(R)-(3,5-bis (trifluoromethyl)phenyl) ethoxy)-4-(5-(dimethylamino) methyl-1,2,3-triazol-4-yl)methyl-3-(S)-phenylmorpholine.

Test Compound B is the less active enantiomer of Test Compound A—i.e. 2-(S)-(1-(R)-(3,5-bis(trifluoromethyl) phenyl)ethoxy)-4-(5-(dimethylamino) methyl-1,2,3-triazol-4-yl)methyl-3-(R)-phenylmorpholine.

Test Compounds A and B were dissolved in 0.9% saline and administered s.c. in the flank. Due to limitations of solubility, fluoxetine was suspended in 0.5% methocel and given i.p. The injection volume was 1 ml/kg.

Results

Guinea-pig pups isolated from their mothers and littermates emitted a vigorous vocalisation response during the first 15 minutes of separation (total duration approximately 8 minutes during this period). Administration of the highly CNS penetrant NK-1 receptor antagonist Test Compound A (0.25 mg/kg s.c.), or fluoxetine (2 mg/kg i.p.) alone 30 minutes previously attenuated separation-induced vocalisations by approximately 25% compared with the baseline vocalisation response determined using the same animals on the previous day. Combined administration of Test Compound A (0.25 mg/kg s.c.) and fluoxetine (2 mg/kg i.p.) virtually abolished separation-induced vocalisations (FIG. 1). The NK-1 receptor specificity of this effect was confirmed by the failure of the less active enantiomer, Test Compound B (0.25 mg/kg s.c.) to attenuate separation-induced vocalisations when administered alone, or to potentiate the inhibitory effect of fluoxetine (2 mg/kg i.p.; FIG. 1).

The above results provide evidence for a synergistic interaction between a centrally acting NK-1 receptor antagonist (Test Compound A) with the anti-obesity drug fluoxetine in a distress vocalisation assay using guinea-pigs. This appears to reflect a specific NK-1 receptor mediated interaction, since co-administration of the less active enantiomer, Test Compound B, at the same dose failed to potentiate the ability of fluoxetine to inhibit vocalisations. The findings provide experimental evidence that centrally acting NK-1 receptor antagonists may augment the therapeutic response to clinically used selective serotonin reuptake inhibitors (such as fluoxetine).

The following assay may be used to demonstrate the potentiation of the anti-obesity effect of SSRIs in diet-induced obese mice when co-administered with a NK-1 receptor antagonist.

Evaluation of the Interaction of NK-1 Antagonists and Selective Serotonin Reuptake Inhibitors on Food Intake and Body Weight in Diet-Induced Obese Mice.

Mice

Male C57BL/J mice were obtained from Jackson Labs at 3 weeks of age. Half the mice were maintained on a wet diet consisting of sweetened condensed milk and standard ground rodent chow (70%:30%, vol:vol). Fresh wet chow was provided daily. These mice will be referred to as diet-induced obese (DIO). The other half was maintained on just ground rodent chow. These will be referred to as Non-Obese Littermates (NOL). Both food and water were supplied ad libitum. Mice were housed with a 12 hour light/dark cycle (4.00 am lights on) through out the course of the described studies.

Mice were weighed biweekly until a point that both DIO and NOL mice were weight stable (approximately 20 weeks). At this time, DIO mice weighed significantly more than NOL mice ($p^2 0.01$). DIO mice also exhibited elevated insulin and glucose levels, as well as polyuria.

Food Intake (All food intake studies are performed on weight stable DIO mice. Both food and water are available before treatment.)

The combined effect that the NK-1 antagonist and the SSRI has on food consumption in DIO mice is examined by observing the resulting changes in food intake observed after treatment with SSRI, NK-1 antagonist, or combinations of SSRI with decreasing doses of NK-1 antagonist.

Mice are randomly assigned to one of the following treatment groups:

Saline/Saline

Saline/NK-1 antagonist @ 20 mg/kg

SSRI @ 3 mg/kg/NK-1 antagonist @ 20 mg/kg

SSRI @ 3 mg/kg/NK-1 antagonist @ 10 mg/kg

SSRI @ 3 mg/kg/NK-1 antagonist @ 5 mg/kg

Mice receive two injections approximately 30 mins apart. All injections are administered ip., in a volume of 0.2 ml between 3.00 pm and 3.30 pm. Fresh chow is provided at the time of injection. Food intake is measured 16 hours post-injection for each mouse.

Results are expressed as inhibition of food intake relative to that of saline treated animals.

Body Weight (All weight studies are performed on DIO mice)

The effect that the combination of SSRIs and NK-1 antagonists have on weight are examined using a chronic dosing regimen. Mice are treated with SSRI, NK-1 antagonist, or combinations of SSRI with decreasing doses of NK-1 antagonist, similar to those used in the evaluation of food intake. Mice are dosed once daily, for 7 days with body weights being measured at the start and conclusion of the study. Changes in body weight are compared with that of saline treated mice.

Concurrent daily food intake measurements may be taken at this time.

The following examples illustrate pharmaceutical compositions according to the invention.

These formulations may be prepared with separate active ingredients or with a combination of active ingredients in one composition. In such combined preparations, the ratio of the NK-1 receptor antagonist and the SSRI will depend upon the choice of active ingredients.

EXAMPLE 1

Tablets containing 50–300mg of NK-1 antagonist and 20mg of fluoxetine

|  | Amount mg | | |
| --- | --- | --- | --- |
| NK-1 antagonist | 50.0 | 100.0 | 300.0 |
| fluoxetine | 20.0 | 20.0 | 20.0 |
| Microcrystalline cellulose | 80.0 | 80.0 | 80.0 |
| Modified food corn starch | 80.0 | 80.0 | 80.0 |
| Lactose | 169.5 | 119.5 | 119.5 |
| Magnesium Stearate | 0.5 | 0.5 | 0.5 |

The active ingredients cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 50 mg, 100 mg and 300 mg of the NK-1 receptor antagonist per tablet.

EXAMPLE 2

Parenteral injection

|  | Amount | |
| --- | --- | --- |
| Active Ingredients | 10 to 300 | mg |
| Citric Acid Monohydrate | 0.75 | mg |
| Sodium Phosphate | 4.5 | mg |
| Sodium Chloride | 9 | mg |
| Water for injection | to 10 | ml |

The sodium phosphate, citric acid monohydrate and sodium chloride are dissolved in a portion of the water. The active ingredients are dissolved or suspended in the solution and made up to volume.

What is claimed is:

1. A method for the treatment or prevention of obesity, which method comprises administration to a patient in need thereof of an amount of a NK-1 receptor antagonist and an amount of a selective serotonin reuptake inhibitor, such that together they give effective relief.

2. The method of claim 1 wherein the NK-1 receptor antagonist is orally active, long acting and CNS-penetrant.

3. The method of claim 1 wherein the NK-1 receptor antagonist is selected from 2-(S)-(3,5-bis(trifluoromethyl)benzyloxy)-3(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-(3-(5-oxo-1H,4H-1,2,4-triazolo)methyl)-3-(S)-phenylmorpholine;

2-(S)-(3,5-bis(trifluoromethyl)benzyloxy)-4-(3-(5-oxo-1H,4H-1,2,4-triazolo)methyl)-3-(S)-phenylmorpholine;

2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine;

2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine;

2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;

2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

2-(R)-(1-(R)-(3,5-bis(trifluoromethyl)phenyl)ethoxy)-4-(4—N,N-dimethylaminobut-2-yn-yl)-3-(S)-(4-fluorophenyl)morpholine;

or a pharmaceutically acceptable salt thereof.

4. The method of claim 1 wherein the selective serotonin reuptake inhibitor is selected from fluoxetine, fluvoxamine, paroxetine and sertraline; or a pharmaceutically acceptable salt thereof.

5. The method of claim 1 wherein the selective serotonin reuptake inhibitor is fluoxetine or a pharmaceutically acceptable salt thereof.

6. The method of claim 1 wherein the selective serotonin reuptake inhibitor is fluvoxamine or a pharmaceutically acceptable salt thereof.

7. The method of claim 1 wherein the selective serotonin reuptake inhibitor is paroxetine or a pharmaceutically acceptable salt thereof.

8. The method of claim 1 wherein the selective serotonin reuptake inhibitor is sertraline or a pharmaceutically acceptable salt thereof.

* * * * *